(12) United States Patent
Li et al.

(10) Patent No.: US 9,265,835 B2
(45) Date of Patent: Feb. 23, 2016

(54) COMPOSITIONS OF ROTIGOTINE, DERIVATIVES THEREOF, OR PHARMACEUTICALLY ACCEPTABLE SALTS OF ROTIGOTINE OR ITS DERIVATIVE

(75) Inventors: Youxin Li, Langenfeld (DE); Aiping Wang, Shandong (CN); Wanhui Liu, Shandong (CN); Kaoxiang Sun, Shandong (CN); Jun Li, Beijing (CN); Lifang Sun, Shandong (CN)

(73) Assignee: SHAN DONG LUYE PHARMACEUTICAL CO., LTD., Shandong (CN)

( * ) Notice: Subject to any disclaimer, the term of this patent is extended or adjusted under 35 U.S.C. 154(b) by 152 days.

(21) Appl. No.: 13/989,550

(22) PCT Filed: Nov. 25, 2011

(86) PCT No.: PCT/CN2011/001958
§ 371 (c)(1),
(2), (4) Date: Aug. 8, 2013

(87) PCT Pub. No.: WO2012/068783
PCT Pub. Date: May 31, 2012

(65) Prior Publication Data
US 2013/0309314 A1 Nov. 21, 2013
US 2014/0377369 A2 Dec. 25, 2014

(30) Foreign Application Priority Data
Nov. 25, 2010 (CN) .......................... 2010 1 0576447

(51) Int. Cl.
| | |
|---|---|
| *A61K 9/50* | (2006.01) |
| *A61K 31/38* | (2006.01) |
| *C07D 333/20* | (2006.01) |
| *A61K 47/34* | (2006.01) |
| *A61K 9/16* | (2006.01) |
| *A61K 31/381* | (2006.01) |

(52) U.S. Cl.
CPC ............... *A61K 47/34* (2013.01); *A61K 9/1617* (2013.01); *A61K 9/1647* (2013.01); *A61K 31/381* (2013.01)

(58) Field of Classification Search
None
See application file for complete search history.

(56) References Cited

U.S. PATENT DOCUMENTS

2009/0105153 A1   4/2009   Thanoo et al.

FOREIGN PATENT DOCUMENTS

| CN | 1762495 A | 4/2006 |
|---|---|---|
| CN | 101467959 A | 7/2009 |
| EP | 1 797 871 A1 | 6/2007 |
| JP | 2001-515862 | 9/2001 |
| JP | 2008-506717 | 3/2008 |
| JP | 2008-513524 | 5/2008 |
| JP | 2009-155302 | 7/2009 |
| KR | 1020070059161 A | 11/2007 |
| WO | WO 99/12549 | 3/1999 |

OTHER PUBLICATIONS

Zhang et al.; CN 1762495; published Apr. 26, 2006; machine translation attached (pdf).*
Ruimei et al.; CN 101467959; published Jul. 1, 2009; machine translation attached (pdf).*
Duvvuri et al.; Pharmaceutical Research, vol. 23, No. 1, published Jan. 2006.*
The Free Dictionary (Medical); definition for "parenteral"; downloaded Mar. 16, 2016.*
English-language International Search Report from the Chinese Patent Office for International Application No. PCT/CN2011/001958, mailing date Mar. 8, 2012
Chung, T.-W., et al., "Different Ratios of Lactide and Glycolide in PLGA Affect the Surface Property and Protein Delivery Charcteristics of the PLGA Microspheres with Hydrophobic Additives", Journal of Microencapsulation, vol. 23, Feb. 2006, pp. 15-27.
Fahmy, T.M., et al., "Surface Modification of Biodegradable Polyesters with Fatty Acid Conjugates for Improved Drug Targeting", Biomaterials, vol. 26 (2005) pp. 5727-5736.
Govender, T., et al., "PLGA Nanoparticles Prepared by Nanoprecipitation: Drug Loading and Release Studies of a Water Soluble Drug", Journal of Controlled Release, vol. 57 (1999) pp. 171-185.
Sun, F., et al., "Studies on the Preparation, Characterization and Pharmacological Evaluation of Tolterodine PLGA Microspheres", International Journal of Pharmaceutics, vol. 397 (2010) pp. 44-49.
Wang, A., et al., "Preparation of Rotigotine-Loaded Microspheres and Their Combination Use with L-DOPA to Modify Dyskineasias in 6-OHDA-Lesioned Rats", Pharmaceutical Research, vol. 29 (2012) pp. 2367-2376.
Gao, X., et al., "Biodegradable PLGA microspheres for injectable drug delivery system," Proceedings on Biomedical Engineering of DUT, vol. 2 (2005), pp. 418-423.

* cited by examiner

*Primary Examiner* — Jeffrey T Palenik
(74) *Attorney, Agent, or Firm* — Finnegan, Henderson, Farabow, Garrett & Dunner LLP

(57) ABSTRACT

The disclosure relates to a composition comprising rotigotine or a pharmaceutically acceptable salt thereof; at least one poly(lactide-co-glycolide) (PLGA); and at least one fatty acid, wherein the at least one fatty acid is at least 0.5% in weight relative to the total weight of the composition. The composition as disclosed herein has significantly reduced burse release effect. The disclosure also provides a method of treating Parkinson's disease comprising administering an effective amount of the composition as disclosed to a subject in need thereof.

27 Claims, 13 Drawing Sheets

COMPOSITIONS OF ROTIGOTINE, DERIVATIVES THEREOF, OR PHARMACEUTICALLY ACCEPTABLE SALTS OF ROTIGOTINE OR ITS DERIVATIVE

This application claims benefits of Chinese Application No. CN201010576447.5, filed on Nov. 25, 2010.

The disclosure relates to a composition of rotigotine, its derivatives, or the pharmaceutically acceptable salts of rotigotine or its derivatives.

Due to the liver first-pass effect, the oral bioavailability of rotigotine is low (about 1%-5%), and thus rotigotine is not suitable for oral administration. At present, the first transdermal patch for treating Parkinson's disease, a transdermal patch under the trademark Neupro® developed by Schwarz Pharma AG, is on the market in Germany, Britain, Australia, etc. However. crystallized rotigotine may be formed during the course of using that product. To solve this problem, cold-chain storage and distribution at a temperature of 2-8° C. are employed, and each prescription must not be longer than one month so as to avoid crystallization, which will apparently increase patients' difficulty in using that product.

CN1762495A discloses a microsphere formulation comprising rotigotine and degradable polymer auxiliary materials. The rotigotine microsphere formulation as disclosed in CN1762495A may achieve the effect of long-acting sustained release, but a problem of burst release may occur. As shown in FIG. 17 (in vivo test, with a drug-loading rate of 8%), FIG. 12 (in vivo test, with a drug-loading rate of 20%), and FIG. 20 (in vivo test, with a drug-loading rate of 40%) of CN1762495A, when the drug-loading rate is 20% or 40%, the burst release effect is obvious. It may also be seen from FIG. 20 (in vivo test, with a drug-loading rate of 40%) and FIG. 19 (in vitro test, with a drug-loading rate of 40%) of CN1762495A that the released amount of rotigotine within one day in the in vitro test is correlated with the burst releasing of the drug in the in vivo test. For the same drug loading rate, the larger the released amount in the in vitro test, the more drug is burst released in vivo.

As an age-related degenerative disease, Parkinson's disease progressively worsens with increasing patients' age. Thus, the administered dosage should be also increased gradually during the treatment. When treating patients with Parkinson's disease in the progressive period, the daily dose intake of the drug will need to be increased significantly. Thus, when treating patients with Parkinson's disease in the progressive period with rotigotine microspheres, the drug-loading rate of the active component should not be too low. Otherwise, to achieve the same therapeutic effect as microspheres having a higher drug-loading rate, microspheres having a lower drug-loading rate would have to be administered in a relatively larger amount, which may cause pain to patients. However, if the drug-loading rate of the microspheres is too high, when administered to patients, the drug may experience a sudden release, which may cause drug overdose.

The present disclosure provides a composition of a drug, such as rotigotine, its derivatives, or the pharmaceutically acceptable salts of rotigotine or its derivatives, which substantially reduces burst releasing of the drug. The composition comprises rotigotine, its derivatives, or the pharmaceutically acceptable salts of rotigotine or its derivatives;
at least one poly(lactide-co-glycolide) (PLGA); and
at least one fatty acid, wherein the at least one fatty acid is at least about 0.5%, e.g., about 1-15%, in weight relative to the total weight of the composition.

In some embodiments, the composition is in the form of microspheres. For example, the particle diameter of microspheres can be about 1-250 microns, e.g., about 10-200 microns.

In some embodiments, the compound is rotigotine, or a pharmaceutically acceptable salt thereof.

In some embodiments, the rotigotine or a pharmaceutically acceptable salt thereof is about 20-40% in weight relative to the total weight of the composition. In one example, the rotigotine or a pharmaceutically acceptable salt thereof may be about 25-35%, about 25-30%, about 20-30%, about 20-35%, about 25-40%, about 30-35%, about 30-40%, or about 35-40% in weight relative to the total weight of the composition. In another example, the rotigotine or a pharmaceutically acceptable salt thereof may be about 21%, 22%, 23%, 24%, 25%, 26%, 28%, 29%, 30%, 31%, 32%, 33%, 34%, 35%, 36%, 37%, 38%, 39%, or 40% in weight relative to the total weight of the composition.

In some embodiments, the at least one PLGA is about 45-79% in weight relative to the total amount of the composition. The at least one PLGA may comprise two, three, four, or five different types of PLGA polymers, which may be different, e.g., in molecular weight and/or polymerization ratio. In one example, the at least one PLGA is about 47.5-77.5%, about 50-77.5%, about 52.5-72.5%, about 55-72.5%, about 55-69%, about 57.5-72.5%, about 57.5-77.5%, about 60-72.5%, about 60-70%, about 62.5-67.5%, about 45-50%, about 47.5-60%, or about 50-60% in weight relative to the total amount of the composition. In another example, the at least one PLGA is about 45%, about 47.5%, about 50%, about 52.5%, about 55%, about 57.5%, about 60%, about 62.5%, about 65%, about 67.5%, about 70%, about 72.5%, about 75%, about 77.5%, about 78%, or about 79% in weight relative to the total amount of the composition.

In some embodiments, the pharmaceutically acceptable salt is formed by rotigotine and an inorganic acid or an organic acid. The inorganic acid may be chosen from hydrochloric acid, sulphuric acid, phosphoric acid, and nitric acid. The organic acid is chosen from citric acid, fumaric acid, maleic acid, acetic acid, benzoic acid, lactic acid, methane sulfonic acid, naphthalene sulfonic acid, and toluene-p-sulfonic acid. For example, the organic acid can be an acidic amino acid, such as glutamic acid and aspartic acid.

In some embodiments, the at least one PLGA is about 5,000-100,000 Da in molecular weight. For example, the at least one PLGA may be about 5,500-99,000 Da, about 6,000-98,000 Da, about 6,500-97,000 Da, about 7,000-96,000 Da, about 7,500-95,000 Da, about 8,000-94,000 Da, about 8,500-93,000 Da, about 9,000-92,000 Da, about 9,500-91,000 Da, about 10,000-90,000 Da, about 10,500-89,000 Da, about 11,000-88,000 Da, about 10,500-87,000 Da, about 11,000-86,000 Da, about 11,500-85,000 Da, about 12,000-84,000 Da, about 12,500-83,000 Da, about 13,000-82,000 Da, about 13,500-81,000 Da, about 14,000-80,000 Da, about 14,500-79,000 Da, about 15,000-78,000 Da, about 15,500-77,000 Da, about 16,000-76,000 Da, about 16,500-75,000 Da, about 17,000-74,000 Da, about 17,500-73,000 Da, about 18,000-72,000 Da, about 18,500-71,000 Da, about 19,000-70,000 Da, about 19,500-69,000 Da, about 20,000-68,000 Da, about 21,000-67,000 Da, about 22,000-66,000 Da, about 23,000-65,000 Da, about 24,000-64,000 Da, about 25,000-63,000 Da, about 26,000-62,000 Da, about 27,000-61,000 Da, about 28,000-60,000 Da, about 29,000-60,000 Da, about 30,000-59,000 Da, about 31,000-58,000 Da, about 32,000-57,000 Da, about 33,000-59,000 Da, about 34,000-58,000 Da, about 35,000-57,000 Da, about 36,000-56,000 Da, about 37,000-55,000 Da, about 38,000-54,000 Da, about 39,000-53,000

Da, about 40,000-52,000 Da, about 41,000-51,000 Da, about 42,000-50,000 Da, about 42,000-49,000 Da, about 43,000-48,000 Da, about 44,000-47,000 Da, or about 45,000-46,000 Da in molecular weight.

In some embodiments, the at least one PLGA has a polymerization ratio of lactide to glycolide ranging from about 95:5 to 5:95. For example, the polymerization ratio of lactide to glycolide can be about 90:10 to 10:90, about 85:15 to 15:85, about 80:20 to 20:80, about 75:25 to 25:75, about 70:30 to 30:70, about 65:35 to 35:65, about 60:40 to 40:60, or about 55:45 to 45:55. For another example, the polymerization ratio of lactide to glycolide can be about 50:50.

In some embodiments, the polymerization ratio of lactide to glycolide ranges from about 75:25 to 25:75.

In some embodiments, the at least one fatty acid is chosen from fatty acids having 8-24 carbon atoms. The at least one fatty acid may be chosen from stearic acid, palmitic acid, oleic acid, decanoic acid, octanoic acid, and lignoceric acid. For example, the at least one fatty acid can be stearic acid.

In some embodiments, the at least one fatty acid is at least 0.5% in weight relative to the total weight of the composition. For example, the at least one fatty acid can be about 1-15%, about 2-15%, about 3-15%, about 4-15%, about 5-15%, about 6-15%, about 7-15%, about 8-15%, about 9-15%, about 10-15%, about 11-15%, about 12-15%, about 13-15%, about 14-15%, about 1-12.5%, about 2-12.5%, about 3-12.5%, about 4-12.5%, about 5-12.5%, about 6-12.5%, about 7-12.5%, about 8-12.5%, about 9-12.5%, about 10-12.5%, about 11-12.5%, about 1-10%, about 2-10%, about 3-10%, about 4-10%, about 5-10%, about 6-10%, about 7-10%, about 8-10%, about 9-10%, about 1-7.5%, about 2-7.5%, about 3-7.5%, about 4-7.5%, about 5-7.5%, about 6-7.5%, about 1-5%, about 2-5%, about 3-5%, about 4-5%, about 1-3%, about 2-3%, about 2-4%, about 3-4% in weight relative to the total weight of the composition. In another example, the at least one fatty acid can be about 1%, about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 10%, about 10.5%, about 11%, about 11.5%, about 12%, about 12.5%, about 13%, about 13.5%, about 14%, about 14.5%, or about 15%.

In some embodiments, rotigotine or a pharmaceutically acceptable salt thereof is about 20-40% in weight relative to the total weight of the composition, the at least one PLGA is about 57.5-72.5%, and the at least one fatty acid is about 2.5-7.5%.

In some embodiments, rotigotine or a pharmaceutically acceptable salt thereof is about 20-40% in weight relative to the total weight of the composition, the at least one PLGA is about 57.5-77.5%, and the at least one fatty acid is about 2.5%.

In some embodiments, rotigotine or a pharmaceutically acceptable salt thereof is about 30% in weight relative to the total weight of the composition, the at least one PLGA is about 55.5-69%, and the at least one fatty acid is about 1-15%.

In some embodiments, rotigotine or a pharmaceutically acceptable salt thereof is about 30% in weight relative to the total weight of the composition, the at least one PLGA is about 62.5-67.5%, and the at least one fatty acid is about 2.5-7.5%.

In some embodiments, the rotigotine or a pharmaceutically acceptable salt thereof is about 30%, the at least one PLGA is about 67.5%, and the fatty acid is about 2.5% relative to the total weight of the composition.

In some embodiments, the at least one PLGA comprises a first PLGA and a second PLGA, wherein the first PLGA has a molecular weight of about 42,000-75,000 Da, the second PLGA has a molecular weight of about 15,000-35,000 Da, and the weight ratio of the first PLGA and the second PLGA is about 95:5 to 5:95.

In some embodiments, the first PLGA has a molecular weight of about 15,000-30,000 Da, about 15,000-25,000 Da, about 15,000-20,000 Da, about 20,000-35,000 Da, about 20,000-30,000 Da, about 20,000-25,000 Da, about 25,000-35,000 Da, about 25,000-30,000 Da, or about 30,000-35,000 Da.

In some embodiments, the second PLGA has a molecular weight of about 45,000-70,000 Da, about 50,000-65,000 Da, about 55,000-60,000 Da, about 45,000-65,000 Da, about 45,000-60,000 Da, about 45,000-55,000 Da, about 45,000-50,000 Da, about 50,000-70,000 Da, about 50,000-55,000 Da, about 60,000-65,000 Da, about 60,000-70,000 Da, about 45,000-75,000 Da, about 50,000-75,000 Da, about 55,000-75,000 Da, about 60,000-75,000 Da, about 65,000-75,000 Da, or about 70,000-75,000 Da.

In some embodiments, the weight ratio of the first PLGA and the second PLGA can be about 90:10 to 10:90, about 85:15 to 15:85, about 80:20 to 20:80, about 75:25 to 25:75, about 70:30 to 30:70, about 65:35 to 35:65, about 60:40 to 40:60, or about 55:45 to 45:55.

In some embodiments, the first PLGA is chosen from PLGA (7525 4A) and PLGA (7525 5A), and the second PLGA is PLGA (5050 2.5A).

In some embodiments, the weight ratio of the first PLGA and the second PLGA is about 50:50.

In some embodiments, the rotigotine or a pharmaceutically acceptable salt thereof is about 20-40%, the amount of the first PLGA and the second PLGA is about 57.5-72.5%, and the fatty acid is about 2.5-7.5% relative to the total weight of the composition.

In some embodiments, the rotigotine or a pharmaceutically acceptable salt thereof is about 20-40%, the amount of the first PLGA and the second PLGA is about 57.5-77.5%, and the fatty acid is about 2.5% relative to the total weight of the composition.

In some embodiments, the rotigotine or a pharmaceutically acceptable salt thereof is about 30%, the amount of the first PLGA and the second PLGA is about 55-69%, and the fatty acid is about 1-15% relative to the total weight of the composition.

In some embodiments, the rotigotine or a pharmaceutically acceptable salt thereof is about 30%, the amount of the first PLGA and the second PLGA is about 62.5-67.5%, and the fatty acid is about 2.5-7.5% relative to the total weight of the composition.

In some embodiments, the rotigotine or a pharmaceutically acceptable salt thereof is about 30%, the amount of the first PLGA and the second PLGA is about 67.5%, and the fatty acid is about 2.5% relative to the total weight of the composition.

The composition as disclosed herein may provide a long-acting sustained release of the compound, such as rotigotine, or a pharmaceutically acceptable salt thereof. For example, a microsphere preparation comprising rotigotine or a pharmaceutically acceptable salt thereof, PLGA, and a fatty acid may reduce the low drug release effect that may occur after the microsphere preparation is administered for 1-4 days and in the meantime have reduced burst release effect. The microspheres prepared as disclosed herein also provide good batch-to-batch consistency. The variation of the drug concentrations in blood among individual animals may also be significantly reduced.

The composition as disclosed herein may reduce the burst release effect, especially when the compound, such as rotigotine, or a pharmaceutically acceptable salt thereof, is above 20% in weight relative to the total weight of the composition. The weight percentage of the compound, such as rotigotine, or a pharmaceutically acceptable salt thereof relative to the total weight of the composition is also referred herein as the "drug-loading rate."

The composition as disclosed herein releases the drug stably in a long term without significant burst release, thus achieving the purpose of long-acting sustained release.

The PLGA as disclosed herein is also known as poly(lactide-co-glycolide), which is a lactide/glycolide copolymer. The polymerization ratio of lactide to glycolide within poly(lactide-co-glycolide) can be any appropriate ratio. For example, the polymerization ratio of lactide to glycolide can be about 95:5 to 5:95, such as about 75:25 to 25:75.

PLGA may be represented by the following structure:

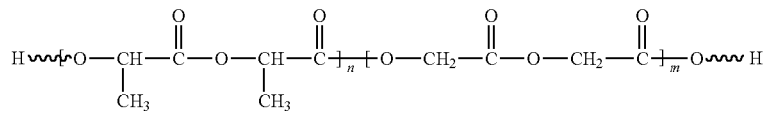

wherein n is zero or a positive integer, and m is zero or a positive integer, but n and m cannot be zero at the same time. The PLGA as disclosed herein may be further chemically modified.

The microspheres as disclosed herein are of a matrix type comprising a drug dissolved and/or dispersed homogeneously throughout a polymer matrix.

The microspheres as disclosed herein may range in size of about 1-250 μm such as about 10-240 μm, about 20-230 μm, about 40-210 μm, about 50-200 μm, about 60-190 μm, about 70-180 μm, about 80-170 μm, about 90-160 μm, about 100-150 μm, about 110-140 μm, or about 120-130 μm. For example, the microspheres as disclosed herein may be about 10, 20, 30, 40, 50, 60, 70, 80, 90, 100, 110, 120, 130, 140, 150, 160, 170, 180, 190, 200, 210, 220, 230, 240, or 250 μm.

The microspheres as disclosed herein may be prepared by any conventional method in the art, including but not limited to, a spray drying method, a solvent volatilization method, or a spray extraction method.

When the microspheres are prepared by the solvent volatilization method, the compound, such as rotigotine, or a pharmaceutically acceptable salt thereof, PLGA and the fatty acid are first dissolved in an organic solvent to prepare an organic phase. A continuous aqueous phase is prepared from water-soluble pharmaceutical polymer auxiliary materials. The organic phase is then injected into the continuous aqueous phase through a small tube to form a mixture, which is emulsified under vigorous mechanical stirring or ultrasonic stirring so as to form microspheres. Next, the organic solvent is evaporated, and the resulting microspheres are filtered and dried. If necessary, the microspheres may also be post-treated by washing, grading, etc., according to a conventional method, dried by vacuum drying or lyophilizing, and finally subpackaged.

In the above processes, the organic solvent may be those with sufficient volatility, low-residue, and low boiling point. For example, the organic solvent may be dichloromethane, chloroform, ethyl acetate, diethyl ether, or any combination thereof. The water-soluble pharmaceutical polymer auxiliary materials used for forming the continuous water phase may be chosen from, but not limited to, polyvinyl alcohol, sodium carboxymethyl cellulose, polyvinyl pyrrolidine, sodium polymethacrylate, sodium polyacrylate, and any combination thereof.

The amounts of the compound, such as rotigotine, or a pharmaceutically acceptable salt thereof, poly(lactide-co-glycolide), and the fatty acid in the organic solvent are not particularly limited, provided that they can be dissolved in the organic solvent. For example, poly(lactide-co-glycolide) and the fatty acid can be about 1-30% (w/v), such as about 5-25% (w/v) or about 10-20% (w/v), in the organic solvent.

When the continuous aqueous phase is prepared from polyvinyl alcohol, sodium carboxymethyl cellulose, polyvinyl pyrrolidine, sodium polymethacrylate, sodium polyacrylate, or any combination thereof, there are no special limits on the concentration of these polymer auxiliary materials. For example, the concentration of these polymer auxiliary materials can be 0.01-12.0% (w/v), such as 0.01-10.0% (w/v), such as 0.1-5% (w/v), in the aqueous phase based on their solubility in water.

When the organic phase is injected into the aqueous phase and stirred vigorously to form the microspheres, the volume ratio of the aqueous phase to the organic phase should be large enough to sufficiently disperse the organic phase in the aqueous phase so as to form the microspheres with sufficiently small particle size and good uniformity. But if the amount of the aqueous phase is more than needed, post-treatment may be complicated, thus increasing cost. For example, the volume ratio of the organic phase to the aqueous phase can be about 1:4 to 1:100, such as about 1:5, about 1:10, about 1:20, about 1:30, about 1:40, about 1:50, about 1:60, about 1:70, about 1:80, about 1:90, or about 1:100.

The microspheres may also be prepared by a spray drying method. For example, the compound, such as rotigotine, or a pharmaceutically acceptable salt thereof, PLGA, and other excipients are dissolved in an organic solvent sufficiently to prepare an organic solution. The organic solution is filtered and dried by a conventional spray drying method to form microspheres. If necessary, the microspheres may also be post-treated by washing, grading, etc., according to conventional method, and then subpackaged.

When microspheres are prepared by the above spray drying method, the organic solvent may be chosen from, but not limited to, dichloromethane, chloroform, ethyl acetate, dioxane, diethyl ether, acetone, tetrahydrofuran, glacial acetic acid, and any combination thereof.

When preparing the organic phase, there are no special limits on the amount of PLGA in the organic solvent, provided that PLGA can be dissolved in the organic solvent. For example, the concentration of PLGA can be about 1-30% (w/v), such as about 5-25% (w/v) or about 10-20% (w/v).

The microspheres may also be prepared by a spray extraction method. When the microspheres are prepared by the spray extraction method, the compound, such as Rotigotine, or a pharmaceutically acceptable salt thereof, PLGA, and other excipients are dissolved sufficiently in an organic solvent A (in which the compound, such as Rotigotine, or a pharmaceutically acceptable salt thereof, PLGA, and fatty acid can be dissolved) to prepare an organic solution. Then the organic solution is sprayed into water or an organic solvent B (in which Rotigotine or a pharmaceutically acceptable salt thereof, PLGA, and fatty acid have limited solubility) and extracted to form microspheres. If necessary, the microspheres may also be post-treated by washing, grading, etc., according to conventional method, and then subpackaged.

The organic solvent A may be at least one chosen from dichloromethane, chloroform, ethyl acetate, dioxane, diethyl ether, acetone, tetrahydrofuran, benzene, toluene, and glacial acetic acid. The organic solvent B may be at least one chosen from methanol, ethanol, propanol, isopropanol, petroleum ether, alkane, and paraffinum liquidum.

There are no special limits on the amount of PLGA in the organic solvent A, provided that PLGA can be dissolved in the organic solvent A. For example, the concentration of PLGA in the organic solvent A can be about 1-30% (w/v), such as about 5-25% (w/v) or about 10-20% (w/v).

In order to improve the uniformity of the particle size of the formed microspheres and for the convenience of handling, the spray drying method may be preferred over the solvent volatilization method and spray extraction method. To lower the initial release, however, the solvent volatilization method may be preferred.

After preparation, the microspheres may be subjected to particle-size grading, cleaning, drying, and subpackaged according to a predetermined dosage to prepare powder injections. If the particle size is of sufficient uniformity, the step of particle-size grading may be eliminated.

The disclosure also provides powder injections prepared using the composition disclosed herein. The powder injections may be converted into injections in situ when in use. The powder injections may be prepared directly from the composition, such as in a microsphere form, as disclosed herein, and mixed uniformly with a sodium carboxymethyl cellulose injectable before use. The powder injections may also be prepared by mixing the composition, such as in a microsphere form, as disclosed herein, with an appropriate amount of sodium carboxymethyl cellulose, mannitol, glucose, etc. An appropriate amount of purified water can be added thereto prior to use to prepare an injectable.

The disclosure also provides a method of treating a disease associated with dopamine receptors and/or Parkinson's disease comprising administering an effective amount of the composition as disclosed herein to a subject in need thereof. For example, the method may comprise administering a composition comprising rotigotine or a pharmaceutically acceptable salt thereof in an amount of about 20-35% in weight relative to the total weight of the composition, at least one fatty acid in an amount of about 2.5-10% in weight relative to the total weight of the composition, and at least one PLGA in an amount of about 55-77.5% in weight relative to the total amount of the composition, wherein the composition is in a form of microspheres. In another example, the method may comprise administering a composition comprising rotigotine or a pharmaceutically acceptable salt thereof in an amount of about 30% in weight relative to the total weight of the composition, at least one fatty acid in an amount of about 2.5% in weight relative to the total weight of the composition, and at least one PLGA, such as a first PLA and a second PLGA as disclosed herein, in an amount of about 67.5% in weight relative to the total amount of the composition, wherein the composition is in a form of microspheres.

The composition as disclosed herein can be administered parenterally to a subject in need thereof. For example, the composition can be administered by intramuscular injection, subcutaneous injection, intradermal injection, intraperitoneal injection, etc. For ease of administration, the composition as disclosed herein can be administered via intramuscular injection or subcutaneous injection.

The composition as disclosed herein may be administered at intervals of at least about two weeks, such as about three weeks, about four weeks, about five weeks, etc.

EXAMPLES

Figure 1:
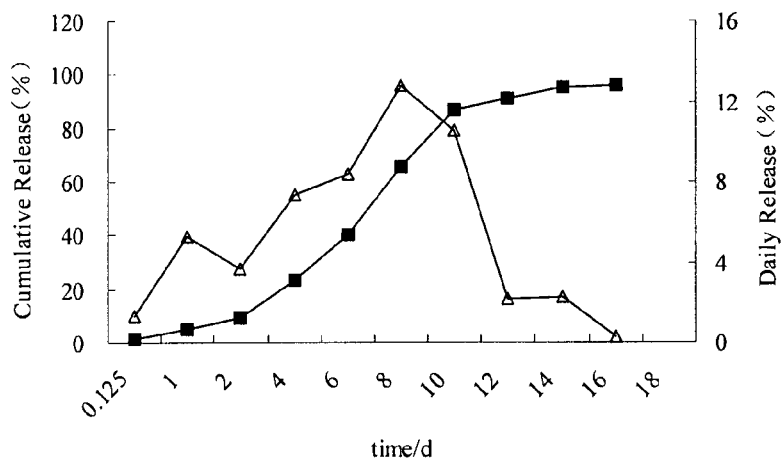
FIG. 1 is the in vitro release diagram of the microspheres (with a theoretical drug-loading rate of 20%) comprising a single PLGA prepared in Example 1, in which Δ represents the daily released amount, and ■ represents the cumulative released amount.
Figure 2:
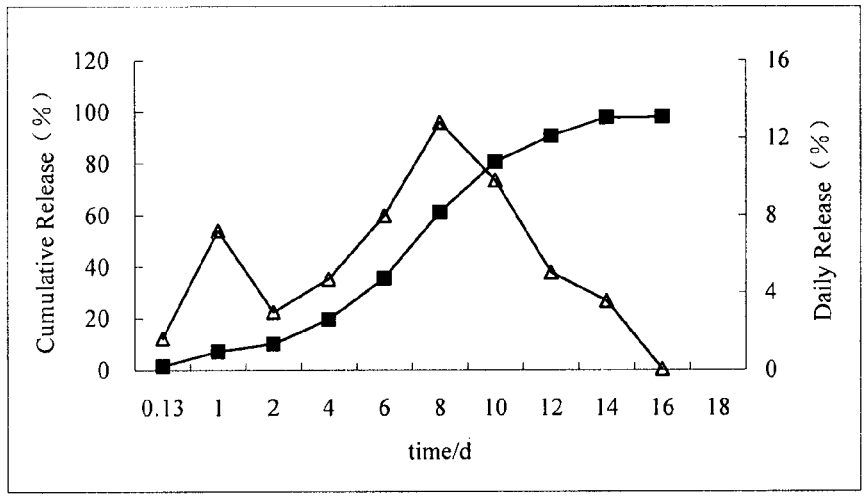
FIG. 2 is the in vitro release diagram of the microspheres (with a theoretical drug-loading rate of 25%) comprising a single PLGA prepared in Example 2, in which Δ represents the daily released amount, and ■ represents the cumulative released amount.
Figure 3:
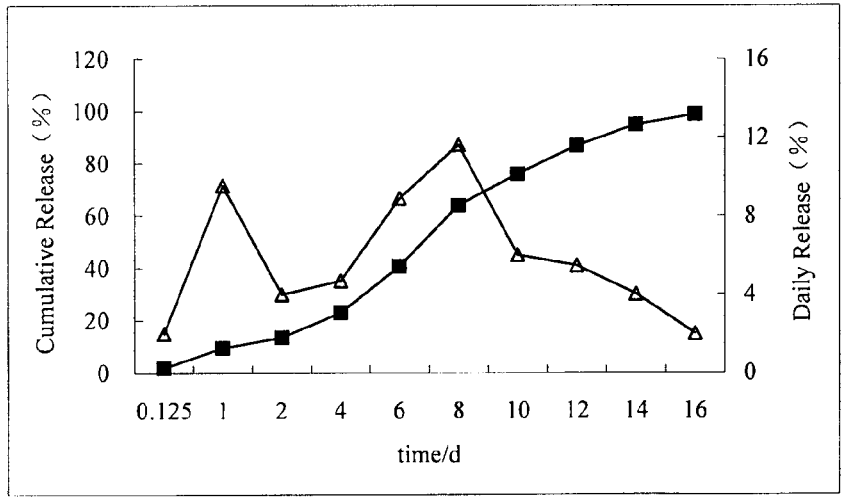
FIG. 3 is the in vitro release diagram of the microspheres (with a theoretical drug-loading rate of 30%) comprising a single PLGA prepared in Example 3, in which Δ represents the daily released amount, and ■ represents the cumulative released amount.
Figure 4:
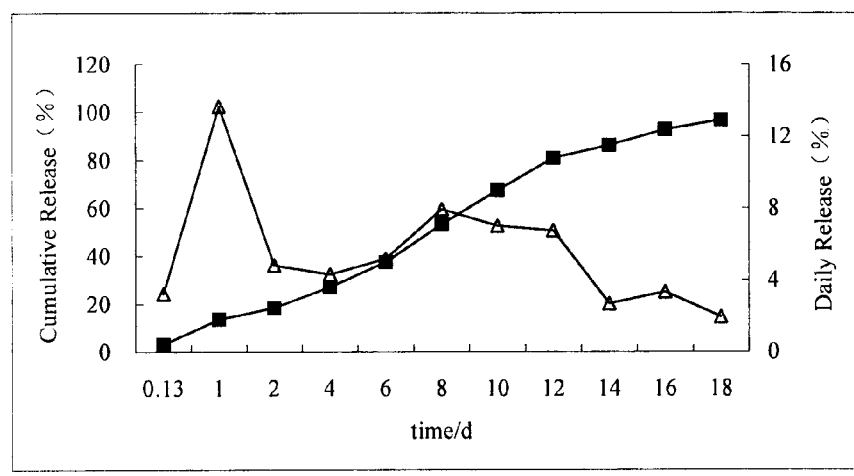
FIG. 4 is the in vitro release diagram of the microspheres (with a theoretical drug-loading rate of 35%) comprising a single PLGA prepared in Example 4, in which Δ represents the daily released amount, and ■ represents the cumulative released amount.
Figure 5:
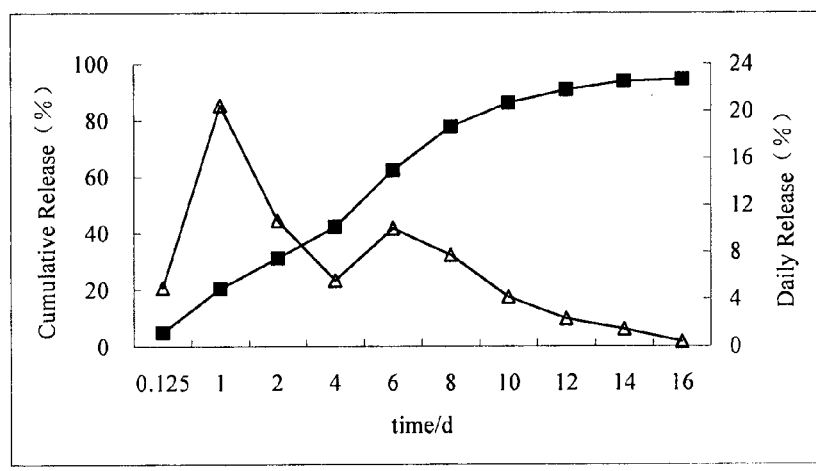
FIG. 5 is the in vitro release diagram of the microspheres (with a theoretical drug-loading rate of 40%) comprising a single PLGA prepared in Example 5, in which Δ represents the daily released amount, and ■ represents the cumulative released amount.

The present disclosure is illustrated further with the following non-limiting examples.

Example 1

Microspheres Comprising a Single PLGA (with a Theoretical Drug-Loading Rate of 20%)

0.3104 g of rotigotine and 1.2083 g of PLGA 7525 4A were weighted out and dissolved in 7.5 mL of dichloromethane with stirring to prepare a mixture. The mixture was added to 750 mL 0.5% PVA aqueous solution by a peristaltic pump (100 rpm) with stirring (1200-2000 rpm), which was emulsified for 2 min. Then the stirring speed was reduced and the solvent was evaporated for 5 hr. The solution obtained was filtered with 1200-mesh sieve to collect the microspheres. The microspheres retained on the 1200-mesh sieve were washed with purified water for 3-5 times, lyophilized, and filtered with 100-mesh sieve to prepare the final microspheres.

Example 2

Microspheres Comprising a Single PLGA (with a Theoretical Drug-Loading Rate of 25%)

The rotigotine microspheres were prepared from 0.3752 g of rotigotine and 1.1291 g of PLGA 7525 4A according to the method of EXAMPLE 1.

Example 3

Microspheres Comprising a Single PLGA (with a Theoretical Drug-Loading Rate of 30%)

The rotigotine microspheres were prepared from 0.4522 g of rotigotine and 1.0511 g of PLGA 7525 4A according to the method of EXAMPLE 1.

Example 4

Microspheres Comprising a Single PLGA (with a Theoretical Drug-Loading Rate of 35%)

The rotigotine microspheres were prepared from 0.5268 g of rotigotine and 0.9790 g of PLGA 7525 4A according to the method of EXAMPLE 1.

Example 5

Microspheres Comprising a Single PLGA (with a Theoretical Drug-Loading Rate of 40%)

The rotigotine microspheres were prepared from 0.6043 g of rotigotine and 0.9019 g of PLGA 7525 4A according to the method of EXAMPLE 1.

Test Example 1

The in vitro release tests were carried out for the microspheres prepared in EXAMPLES 1-5 by simulating the in vivo condition.

Test Condition: temperature: 37±0.5° C., rotation speed: 50 rpm

Chromatographic Condition And System Suitability Protocol: Stearyl bonded silica was used as a filler. 0.3% phosphoric acid-acetonitrile (66:34) were used as a mobile phase, in which 0.3% phosphoric acid was prepared by diluting 3 mL of phosphoric acid with water to final volume of 1000 mL. The column temperature was 35° C. The detection wavelength was 223 nm. The resolution between the rotigotine peak and other peaks should meet the requirements. Theoretical plate number calculated by the rotigotine peak was more than 10000.

Test Method: Assays according to the Drug Release test (Chinese Pharmacopeia 2005, vol. II, appendix X D). 3 aliquots of 6 mg of the microspheres were placed in a centrifuge tube with a plug (10 mL), respectively. To the centrifuge tube was added 9 mL of a release medium of phosphate buffer containing 0.2% SDS. After shaking to suspension, each centrifuge tube was placed in a water bath shaker at 37±0.5° C., and vibrated at a speed of 50±3 rpm. After 3 hr, 1 d, 2 d, 4 d, 6 d, 8 d, 10 d, 12 d, 14 d, 16 d, 18 d, and 20 d, respectively, the centrifuge tubes were taken out. At 5-8° C., the centrifuge tubes were centrifuged at a rotation speed of 3600 rpm for 10 min. Then 6 mL of supernatant was taken out from each centrifuge tube and used as a test solution, and 6.0 mL of a release medium of phosphate buffer at the same temperature was added to the centrifuge tube. After shaking to suspension, the centrifuge tube was placed back in a water bath shaker and vibrated. The above test solution was analyzed by HPLC, and the cumulative released amount was calculated according to the external standard method. Under pH 7.4, the in vitro release data are shown in Table 1, and the in vitro release curves are shown in FIGS. 1-5.

TABLE 1

The results of different theoretical drug-loading rates

| | Drug-loading rate | | | | | | | | | |
|---|---|---|---|---|---|---|---|---|---|---|
| | 20% | | 25% | | 30% | | 35% | | 40% | |
| Time (day) | Cumulative released amount (%) | Daily released amount (%) | Cumulative released amount (%) | Daily released amount (%) | Cumulative released amount (%) | Daily released amount (%) | Cumulative released amount (%) | Daily released amount (%) | Cumulative released amount (%) | Daily released amount (%) |
| 0.125 | 1.33 | 1.33 | 1.63 | 1.63 | 2.00 | 2.00 | 3.24 | 3.24 | 4.97 | 4.97 |
| 1 | 5.24 | 5.24 | 7.19 | 7.19 | 9.53 | 9.53 | 13.65 | 13.65 | 20.45 | 20.45 |
| 2 | 8.87 | 3.63 | 10.18 | 2.99 | 13.53 | 4.00 | 18.47 | 4.82 | 31.14 | 10.69 |
| 4 | 23.61 | 7.37 | 19.55 | 4.69 | 22.90 | 4.68 | 27.1 | 4.32 | 42.30 | 5.58 |
| 6 | 40.39 | 8.39 | 35.48 | 7.97 | 40.65 | 8.88 | 37.44 | 5.17 | 62.32 | 10.01 |
| 8 | 65.91 | 12.76 | 61.06 | 12.79 | 63.87 | 11.61 | 53.3 | 7.93 | 77.80 | 7.74 |
| 10 | 86.91 | 10.50 | 80.66 | 9.80 | 75.85 | 5.99 | 67.32 | 7.01 | 86.18 | 4.19 |
| 12 | 91.18 | 2.14 | 90.72 | 5.03 | 86.74 | 5.44 | 80.8 | 6.74 | 90.86 | 2.34 |
| 14 | 95.63 | 2.22 | 97.85 | 3.57 | 94.75 | 4.01 | 86.18 | 2.69 | 93.79 | 1.47 |
| 16 | 96.22 | 0.30 | 97.99 | 0.07 | 98.74 | 2.00 | 92.86 | 3.34 | 94.56 | 0.38 |
| 18 | | | | | | | 96.79 | 1.97 | | |

The released amounts of rotigotine in 0.125 day and 1 day correlated with the burst release of the drug in vivo. The larger the release amount in vitro, the larger the burst release in vivo.

It may be seen from Table 1 and FIGS. 1-5 that, with the drug-loading rate of the microspheres increased from 20% to 40%, the released amount of rotigotine in 0.125 day was increased from 1.33% to 4.97%, and the cumulative released amount of rotigotine within 1 day was increased from 5.24% to 20.45%. That is, the drug release of the microspheres at the time points of 0.125 day and 1 day were increased significantly. It may be seen from Table 1 that, with the increasing of the drug-loading rate, the burst release of the rotigotine microspheres in vivo may be increased.

Test Example 2

The In Vivo Release Test of the Rotigotine Microspheres

Sample: the microspheres prepared in EXAMPLE 3

Treatment of the plasma sample: 100 µL of an internal standard solution (500ng/mL diazepam), 100 µL of acetonitrile:water (75:25), and 100 µL of 1 M $Na_2CO_3$, agitated for 2 min using a vortex agitator. 3 mL of extracting reagent (n-hexane:dichloromethane:isopropanol=2:1:0.1) was added to the mixture, agitated for 10 min using a vortex agitator and centrifuged for 10 min (3600 $rmin^{-1}$), The organic phase of upper layer was placed in another test tube and dried under a compressed air stream at 35° C. The residue was dissolved in 100 µL of acetonitrile:water (1 mM ammonium acetate)(75:25). 10 µL of the solution was taken as sample injection, and the chromatograms were recorded.

Chromatographic condition: Mobile phase (A): (1 mM NH4Ac) water (B): acetonitrile; gradient elute for 0-0.8 min: B 70~90%. 0.8~3.5 min: B 90~90%, 3.5~3.6 min: B 90~70%, 3.6~7.5 min: B 70~70%; flow rate: 0.35 ml/min column temperature: 35° C.; sample size: 10 µL.

Mass Spectrum Condition

Ion source: ion spray ionization source; ion spray voltage: 5500 V; temperature: 500° C.; GS1: 50 psi; GS2: 50 psi; the pressure of curtain gas (CUR) in the source: 15 psi; the pressure of collision gas (CAD): 8 psi; cation detection mode; scanning mode: multiple reaction monitoring (MRM); DP voltage of Rotigotine and diazepam are separately 50V and 88V; CE are separately 36V and 47V; CXP are both 10V; the ionic reaction for quantitative analysis are separately 316.2/147.1 (rotigotine) and 256.1/167.1 (diazepam).

Creating Work Curve 0.2 mL of blank plasma was added to 100 µL of rotigotine standard solution and 100 µL of internal standard (500 ng/ml diazepam) to prepare plasma samples corresponding to plasma concentrations of 0.05, 0.25, 1.00, 2.50, 1.00, 2.50, 5.00 and 12.5 ng/mL, respectively. The plasma samples were operated according to "the analyzing method of the plasma sample" in Chinese Pharmacopeia 2005, vol. II to create standard curves. Using the concentration of the substance to be examined in the plasma as the x axis, and using the peak area ratio of the substance to be examined to the internal standard substance as the y axis, regression calculation on the standard curves were created according to the weighted ($W=1/x^2$) least squares method to obtain the linear regression equation as the standard curve.

Figure 6:
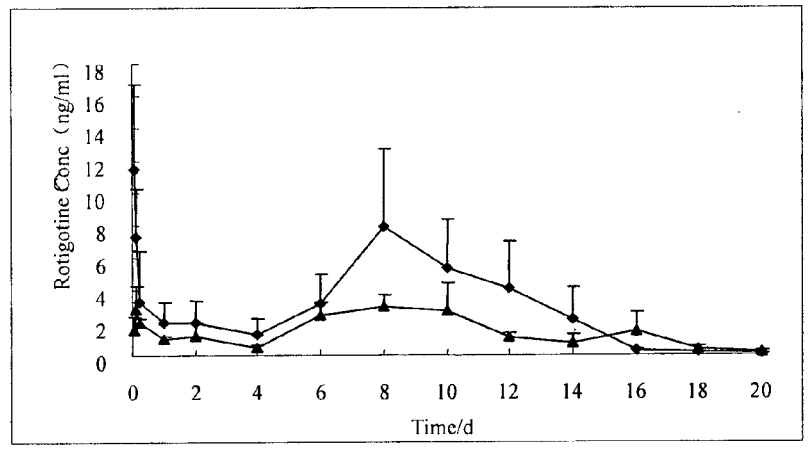
FIG. 6 shows the in vivo concentration curves of the microspheres prepared in Example 3 and Example 8, in which ♦ represents the in vivo release drug-time curve of the microspheres (PLGA 7525 4A) prepared in Example 3, and ▲ represents the in vivo release drug-time curve of the microspheres (containing 2.5% stearic acid and PLGA 7525 4A) prepared in Example 8.
Figure 7:
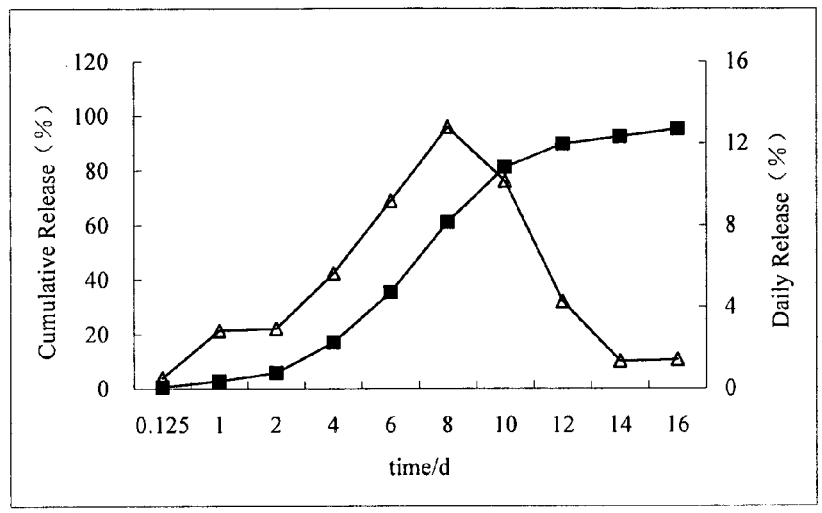
FIG. 7 is the in vitro release diagram of the microspheres (with a theoretical drug-loading rate of 20%) comprising a single PLGA and stearic acid prepared in Example 6, in which Δ represents the daily released amount, and ■ represents the cumulative released amount.
Figure 8:
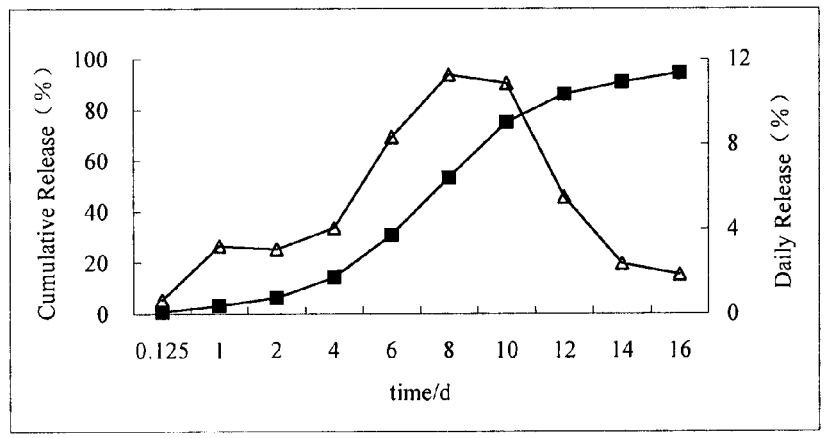
FIG. 8 is the in vitro release diagram of the microspheres (with a theoretical drug-loading rate of 25%) comprising a single PLGA and stearic acid prepared in Example 7, in which Δ represents the daily released amount, and ■ represents the cumulative released amount.
Figure 9:
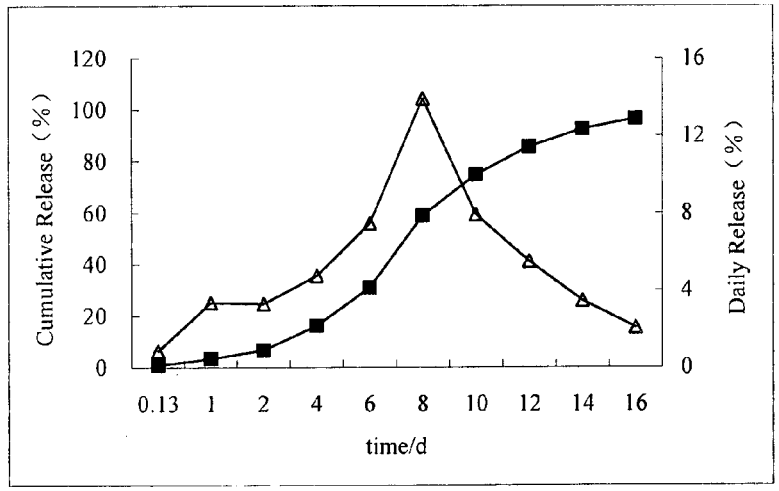
FIG. 9 is the in vitro release diagram of the microspheres (with a theoretical drug-loading rate of 30%) comprising a single PLGA and stearic acid prepared in Example 8, in which Δ represents the daily released amount, and ■ represents the cumulative released amount.
Figure 10:
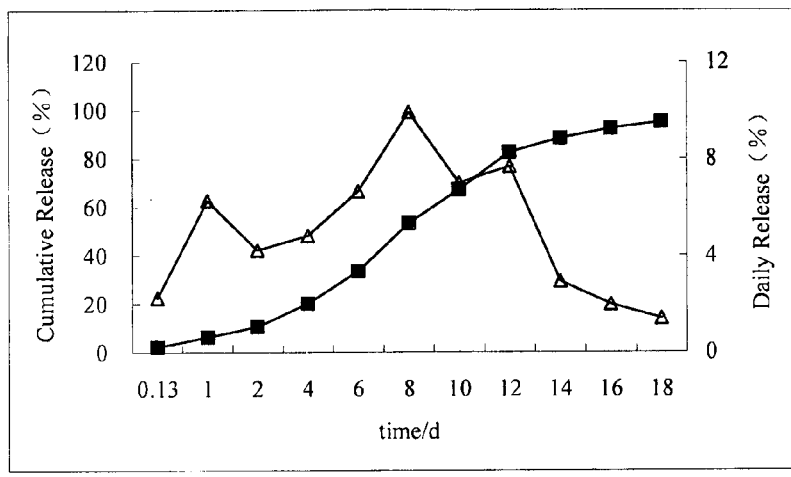
FIG. 10 is the in vitro release diagram of the microspheres (with a theoretical drug-loading rate of 35%) comprising a single PLGA and stearic acid prepared in Example 9, in which Δ represents the daily released amount, and ■ represents the cumulative released amount.
Figure 11:
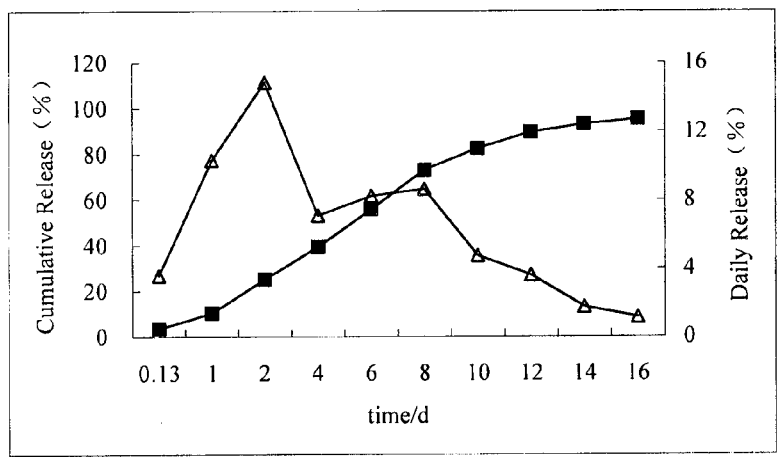
FIG. 11 is the in vitro release diagram of the microspheres (with a theoretical drug-loading rate of 40%) comprising a single PLGA and stearic acid prepared in Example 10, in which Δ represents the daily released amount, and ■ represents the cumulative released amount.

Test Method 3 healthy beagles dogs, one-female and two-males, with a body weight of 9-11 kg, were given food and drinking water ad libitum. The microspheres with a dose of 5.5 mg/kg of rotigotine were administered by injection via the muscle of the beagle, and after administration at 0 hr, 1 hr, 3 hr, 6 hr, 24 hr, 48 hr, 96 hr, 144 hr, 192 hr, 240 hr, 288 hr, 336 hr, 384 hr, 432 hr, and 480 hr, 3 mL of blood was sampled via the forelimb vein of the beagles, placed in a heparinized test tube, centrifuged for 10 min at 6000 rpm, separating plasma, and stored at −20° C. The plasma was analyzed according to the above analytical method, and the in vivo release is shown in FIG. 6. As indicated in Table 1, the cumulative released amount of the microspheres prepared in EXAMPLE 3 within 0.125 day and 1 day were 2.00% and 9.53% respectively. It may be seen from FIG. 6 that, there was an apparent burst release of the microspheres in the body of the beagles, then the blood drug level decreased; after 96 hr, the blood drug level increased, and after 192 hr, the blood drug level increased to $C_{max}$. The blood drug levels at 0.125 day and 1 day were higher than $C_{max}$, which indicates that there was an apparent burst release in the microspheres prepared in EXAMPLE 3.

Example 6

Microspheres Comprising a Single PLGA and Stearic Acid (with a Theoretical Drug-Loading Rate of 20%)

The rotigotine microspheres were prepared from 0.3104 g of rotigotine, 1.1603 g of PLGA 7525 4A and 0.0370 g of stearic acid according to the method of EXAMPLE 1.

Example 7

Microspheres Comprising a Single PLGA and Stearic Acid (with a Theoretical Drug-Loading Rate of 25%)

The rotigotine microspheres were prepared from 0.3712 g of rotigotine, 1.0891 g of PLGA 7525 4A and 0.0379 g of stearic acid according to the method of EXAMPLE 1.

Example 8

Microspheres Comprising a Single PLGA and Stearic Acid (with a Theoretical Drug-Loading Rate of 30%)

The rotigotine microspheres were prepared from 0.4522 g of rotigotine, 1.0136 g of PLGA 7525 4A and 0.0371 g of stearic acid according to the method of EXAMPLE 1.

Example 9

Microspheres Comprising a Single PLGA and Stearic Acid (with a Theoretical Drug-Loading Rate of 35%)

The rotigotine microspheres were prepared from 0.5258 g of rotigotine, 0.9790 g of PLGA 7525 4A and 0.0374 g of stearic acid according to the method of EXAMPLE 1.

Example 10

Microspheres Comprising a Single PLGA and Stearic Acid (with a Theoretical Drug-Loading Rate of 40%)

The rotigotine microspheres were prepared from 0.6083 g of rotigotine, 0.8619 g of PLGA 7525 4A and 0.0367 g of stearic acid according to the method of EXAMPLE 1.

Test Example 3

The in vitro release tests were carried out for the microspheres prepared in EXAMPLES 6-10 according to the method of Test EXAMPLE 1. The in vitro release data are shown in Table 2, and the in vitro release curves are shown in FIGS. 7-11.

TABLE 2

The assay results of different theoretical drug-loading rates containing stearic acid

| | Drug-loading rate | | | | | | | | | |
|---|---|---|---|---|---|---|---|---|---|---|
| | 20% (Stearic acid 2.5%) | | 25% (Stearic acid 2.5%) | | 30% (Stearic acid 2.5%) | | 35% (Stearic acid 2.5%) | | 40% (Stearic acid 2.5%) | |
| Time (day) | Cumulative released amount (%) | Daily released amount (%) | Cumulative released amount (%) | Daily released amount (%) | Cumulative released amount (%) | Daily released amount (%) | Cumulative released amount (%) | Daily released amount (%) | Cumulative released amount (%) | Daily released amount (%) |
| 0.125 | 0.51 | 0.51 | 0.64 | 0.64 | 0.84 | 0.84 | 2.24 | 2.24 | 3.58 | 3.58 |
| 1 | 2.84 | 2.84 | 3.19 | 3.19 | 3.35 | 3.35 | 6.27 | 6.27 | 10.29 | 10.29 |
| 2 | 5.77 | 2.93 | 6.24 | 3.05 | 6.64 | 3.28 | 10.49 | 4.22 | 25.14 | 14.85 |
| 4 | 17.02 | 5.63 | 14.34 | 4.05 | 16.12 | 4.74 | 20.12 | 4.82 | 39.27 | 7.07 |
| 6 | 35.39 | 9.19 | 30.99 | 8.33 | 31.00 | 7.44 | 33.44 | 6.66 | 55.68 | 8.21 |
| 8 | 60.97 | 12.79 | 53.52 | 11.27 | 58.82 | 13.91 | 53.3 | 10 | 72.89 | 8.61 |
| 10 | 81.24 | 10.14 | 75.23 | 10.86 | 74.63 | 7.91 | 67.32 | 7.01 | 82.34 | 4.73 |
| 12 | 89.75 | 4.26 | 86.24 | 5.51 | 85.60 | 5.48 | 82.68 | 7.68 | 89.51 | 3.59 |
| 14 | 92.45 | 1.35 | 90.95 | 2.36 | 92.50 | 3.45 | 88.53 | 2.93 | 92.97 | 1.73 |
| 16 | 95.29 | 1.42 | 94.64 | 1.85 | 96.63 | 2.06 | 92.49 | 1.98 | 95.26 | 1.15 |
| 18 | 97.65 | 1.18 | | | 98.20 | 0.79 | 95.28 | 1.40 | 96.34 | 0.54 |

The data in Table 2 were compared with the data in Table 1. With stearic acid, for the rotigotine microspheres having drug-loading rates of 20%-40%, the released amount of rotigotine in 0.125 day was reduced from 1.33%-4.97% to 0.51%-3.58%, and the cumulative released amount of rotigotine within 1 day was reduced from 5.24%-20.45% to 2.84%-10.29%. This indicates that the addition of stearic acid may effectively reduce the burst release effect.

Test Example 4

In Vivo Release Test of Rotigotine Microspheres

Sample: the microspheres prepared in EXAMPLE 8

The in vivo pharmacokinetics tests were carried out according to the method of Test EXAMPLE 2. The release is shown in FIG. 6. It may be seen from FIG. 6 that, after adding stearic acid, the burst release effect was reduced, however, the drug release amounts in 1-4 days were low.

Example 11

Microspheres Comprising Octanoic Acid and a Single PLGA

The rotigotine microspheres were prepared from 0.4520 g of rotigotine, 1.0119 g of PLGA 7525 4A and 0.0371 g of octanoic acid (2.5%) according to the method of EXAMPLE 1.

Example 12

Microspheres Comprising Lignoceric Acid and a Single PLGA

The rotigotine microspheres were prepared from 0.4489 g of rotigotine, 1.0130 g of PLGA 7525 4A and 0.0373 g of lignoceric acid (2.5%) according to the method of EXAMPLE 1.

Test Example 5

Figure 12:
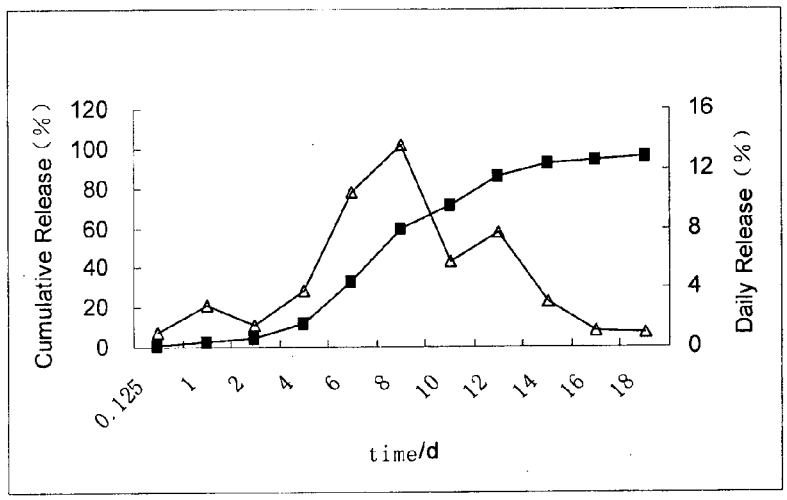
FIG. 12 is the in vitro release diagram of the microspheres comprising 2.5% octanoic acid (C8) prepared in Example 11, in which Δ represents the daily released amount, and ■ represents the cumulative released amount.
Figure 13:
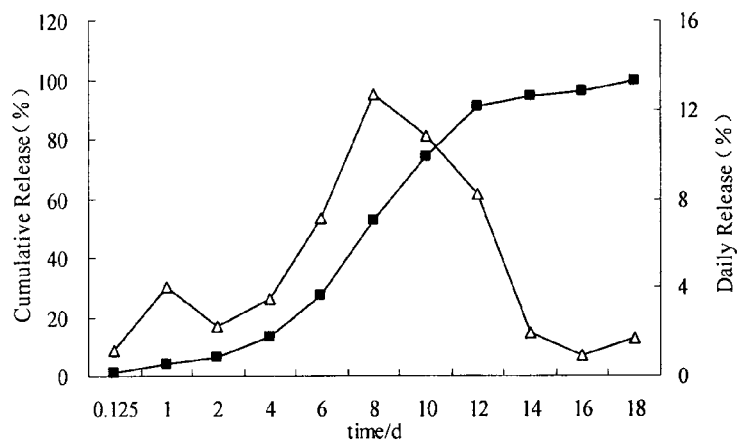
FIG. 13 is the in vitro release diagram of the microspheres comprising 2.5% lignoceric acid (C24) prepared in Example 12, in which Δ represents the daily released amount, and ■ represents the cumulative released amount.
Figure 14:
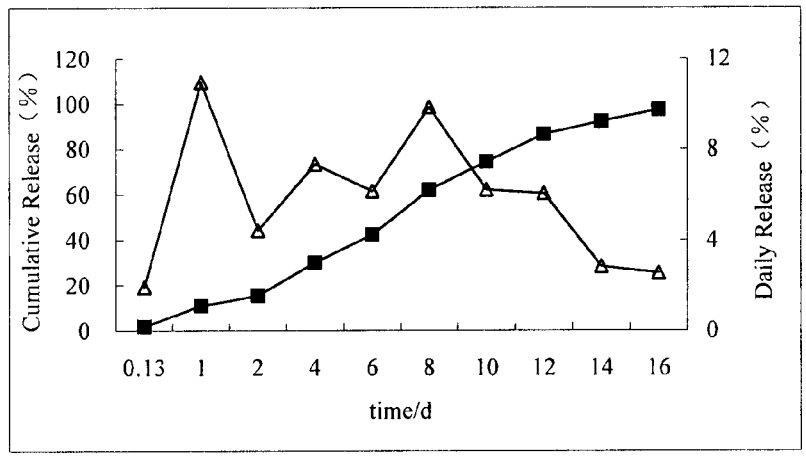
FIG. 14 is the in vitro release diagram of the microspheres comprising 0.5% stearic acid prepared in Example 13, in which Δ represents the daily released amount, and ■ represents the cumulative released amount.
Figure 15:
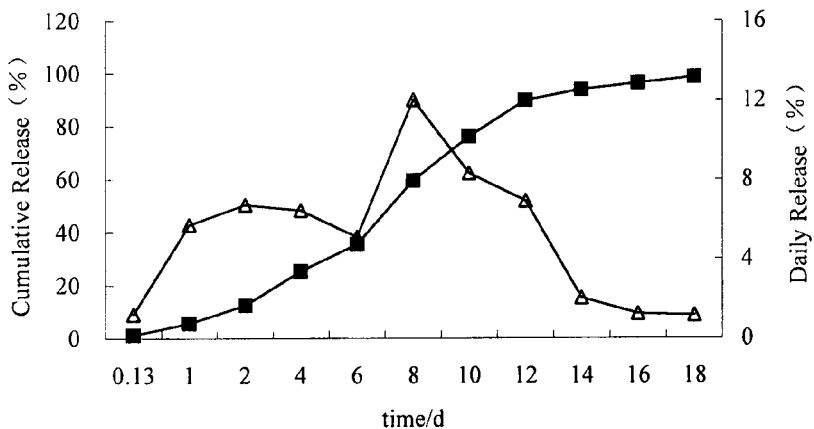
FIG. 15 is the in vitro release diagram of the microspheres comprising 1% stearic acid prepared in Example 14, in which Δ represents the daily released amount, and ■ represents the cumulative released amount.
Figure 16:
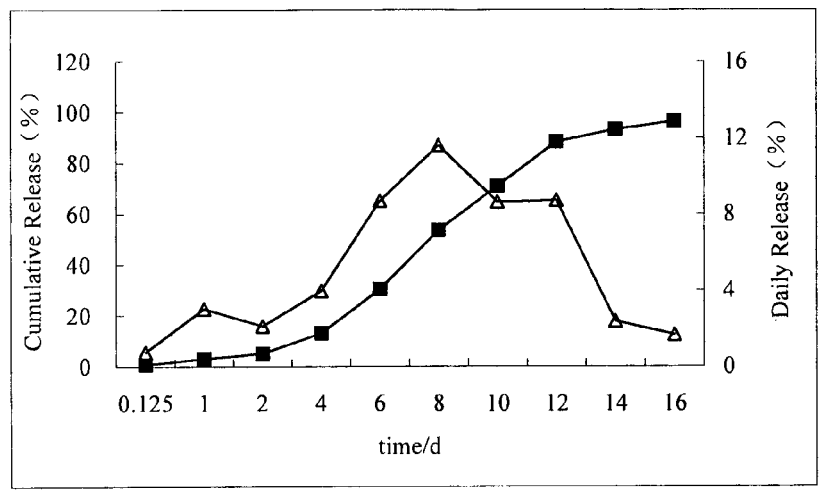
FIG. 16 is the in vitro release diagram of the microspheres comprising 5% stearic acid prepared in Example 15, in which Δ represents the daily released amount, and ■ represents the cumulative released amount.
Figure 17:
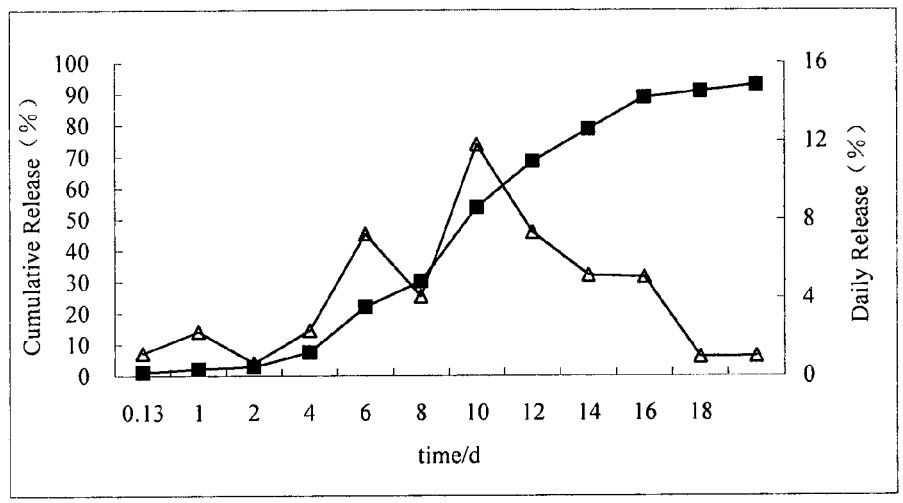
FIG. 17 is the in vitro release diagram of the microspheres comprising 10% stearic acid prepared in Example 16, in which Δ represents the daily released amount, and ■ represents the cumulative released amount.
Figure 18:
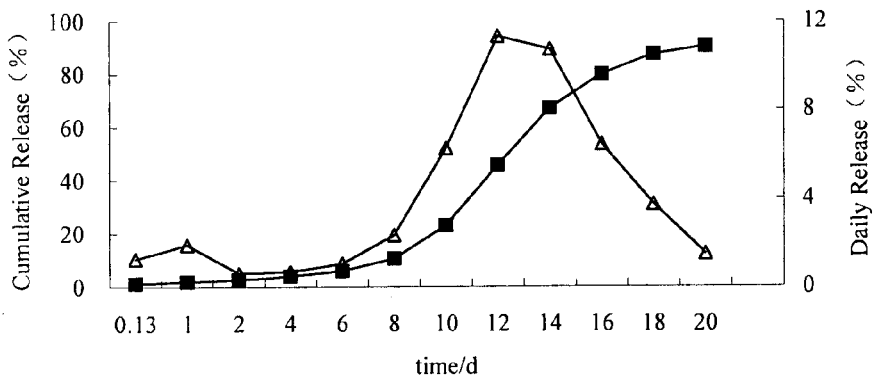
FIG. 18 is the in vitro release diagram of the microspheres comprising 15% stearic acid prepared in Example 17, in which Δ represents the daily released amount, and ■ represents the cumulative released amount.

Influence of Fatty Acids Having Different Numbers of Carbon Atoms on Drug Release of the Rotigotine Microspheres The in vitro release tests were carried out for the microspheres prepared in EXAMPLES 11-12 according to the method of Test EXAMPLE 1. The in vitro release data are shown in Table 3, and the in vitro release curves are shown in FIGS. 12-13.

TABLE 3

The results of the rotigotine microspheres comprising fatty acids having different numbers of carbon atoms

| | 7525 4A 2.5% octanoic acid (C8) | | 7525 4A 2.5% lignoceric acid (C24) | |
|---|---|---|---|---|
| Time (day) | Cumulative released amount (%) | Daily released amount (%) | Cumulative released amount (%) | Daily released amount (%) |
| 0.125 | 1.01 | 1.01 | 1.14 | 1.14 |
| 1 | 2.84 | 2.84 | 4.02 | 4.02 |
| 2 | 4.35 | 1.51 | 6.25 | 2.23 |
| 4 | 11.91 | 3.78 | 13.23 | 3.49 |
| 6 | 32.64 | 10.36 | 27.50 | 7.14 |
| 8 | 59.65 | 13.51 | 52.89 | 12.70 |
| 10 | 71.05 | 5.70 | 74.47 | 10.79 |
| 12 | 86.32 | 7.64 | 90.87 | 8.20 |
| 14 | 92.34 | 3.01 | 94.66 | 1.90 |
| 16 | 94.65 | 1.16 | 96.48 | 0.91 |
| 18 | 96.58 | 0.96 | 99.82 | 1.67 |

The data in Table 3 were compared with the data in Table 1 (with a drug-loading rate of 30%). Compared to rotigotine microspheres without fatty acids, for the rotigotine microspheres with octanoic acid (8 carbon atoms) and lignoceric acid (24 carbon atoms), the released amount of rotigotine in 0.125 day was reduced from 2.00% to 1.01%-1.14%, and the cumulative released amount of rotigotine within 1 day was reduced from 9.53% to 2.84%-4.02%. This indicates that the addition of both octanoic acid and lignoceric acid may effectively reduce the burst release effect. It may be seen from the results in Table 2 (stearic acid having 18 carbon atoms) and Table 3 that, all of the fatty acids having 8-24 carbon atoms may effectively reduce the burst release effect.

Example 13

Microspheres Comprising a Single PLGA and 0.5% Stearic Acid

The rotigotine microspheres were prepared from 0.4528 g of rotigotine, 1.0432 g of PLGA 7525 4A and 0.0078 g of stearic acid (0.5%) according to the method of EXAMPLE 1.

Example 14

Microspheres Comprising a Single PLGA and 1% Stearic Acid

The rotigotine microspheres were prepared from 0.4528 g of rotigotine, 1.0362 g of PLGA 7525 4A and 0.0158 g of stearic acid (1%) according to the method of EXAMPLE 1.

Example 15

Microspheres Comprising a Single PLGA and 5% Stearic Acid

The rotigotine microspheres were prepared from 0.4528 g of rotigotine, 0.9751 g of PLGA 7525 4A and 0.0758 g of stearic acid (5%) according to the method of EXAMPLE 1.

Example 16

Microspheres Comprising a Single PLGA and 10% Stearic Acid

The rotigotine microspheres were prepared from 0.4492 g of rotigotine, 0.9028 g of PLGA 7525 4A and 0.1532 g of stearic acid (10%) according to the method of EXAMPLE 1.

Example 17

Microspheres Comprising a Single PLGA and 15% Stearic Acid

The rotigotine microspheres were prepared from 0.4528 g of rotigotine, 0.8261 g of PLGA 7525 4A and 0.2258 g of stearic acid (15%) according to the method of EXAMPLE 1.

Test Example 6

The in vitro release tests were carried out for the microspheres prepared in EXAMPLEs 13-17 according to the method of Test EXAMPLE 1.

The in vitro release results are shown in Table 4 and FIGS. 14-18.

TABLE 4

The results of the rotigotine microspheres comprising different contents of stearic acid

| Time (day) | 0.5% Stearic acid | | 1% Stearic acid | | 5% Stearic acid | | 10% Stearic acid | | 15% Stearic acid | |
|---|---|---|---|---|---|---|---|---|---|---|
| | Cumulative released amount (%) | Daily released amount (%) | Cumulative released amount (%) | Daily released amount (%) | Cumulative released amount (%) | Daily released amount (%) | Cumulative released amount (%) | Daily released amount (%) | Cumulative released amount (%) | Daily released amount (%) |
| 0.125 | 1.91 | 1.91 | 1.20 | 1.20 | 0.75 | 0.75 | 1.16 | 1.16 | 1.26 | 1.26 |
| 1 | 10.96 | 10.96 | 5.70 | 5.70 | 3.02 | 3.02 | 2.25 | 2.25 | 1.90 | 1.90 |
| 2 | 15.39 | 4.43 | 12.41 | 6.72 | 5.14 | 2.12 | 2.89 | 0.64 | 2.51 | 0.60 |
| 4 | 30.08 | 7.34 | 25.28 | 6.43 | 13.06 | 3.96 | 7.52 | 2.32 | 3.85 | 0.67 |
| 6 | 42.41 | 6.16 | 35.45 | 5.09 | 30.47 | 8.70 | 22.02 | 7.25 | 5.94 | 1.04 |
| 8 | 62.09 | 9.84 | 59.46 | 12.00 | 53.68 | 11.61 | 30.15 | 4.06 | 10.58 | 2.32 |
| 10 | 74.55 | 6.23 | 76.06 | 8.30 | 70.96 | 8.64 | 53.79 | 11.82 | 23.07 | 6.24 |
| 12 | 86.67 | 6.06 | 89.89 | 6.91 | 88.44 | 8.74 | 68.48 | 7.34 | 45.68 | 11.30 |
| 14 | 92.35 | 2.84 | 93.96 | 2.04 | 93.18 | 2.37 | 78.77 | 5.15 | 67.12 | 10.72 |
| 16 | 97.43 | 2.54 | 96.42 | 1.23 | 96.51 | 1.67 | 88.89 | 5.06 | 79.97 | 6.42 |
| 18 | | | 98.73 | 1.16 | | | 90.88 | 0.99 | 87.42 | 3.73 |
| 20 | | | | | | | 92.91 | 1.02 | 90.38 | 1.48 |

It may be seen by comparing the data in Table 4 with the data in Table 1 that, when the content of stearic acid was 0.5%, the released amount of rotigotine in 0.125 day and the cumulative released amount of rotigotine within 1 day were 1.91% and 10.96% respectively, and were not changed significantly compared with the microspheres without stearic acid prepared in EXAMPLE 3. This indicates that the addition of stearic acid with a content of less than or equal to 0.5% may not significantly reduce the burst release effect. When the content of stearic acid was above 0.5%. e.g., 1-15%, the released amount of rotigotine in 0.125 day and the cumulative released amount of rotigotine within 1 day for the microspheres comprising 1 to 15% of stearic acid were reduced to 0.75%-1.26% and 1.90%-5.70% respectively, thus effectively reduced the burst release of the drug. As indicated in the data in Table 4 and FIGS. 14-18, with increasing amount of stearic acid, the release of the drug was slowed down.

Test Example 7

In Vivo Test of the Microspheres Comprising PLGA 5050 2.5 A

The in vivo test was carried out for the microspheres prepared in EXAMPLE 3 comprising PLGA 5050 2.5 A instead of PLGA 7525 4A according to the method of Test EXAMPLE 2, all other things being equal or held constant. The results are shown in FIG. 19.

Figure 19:
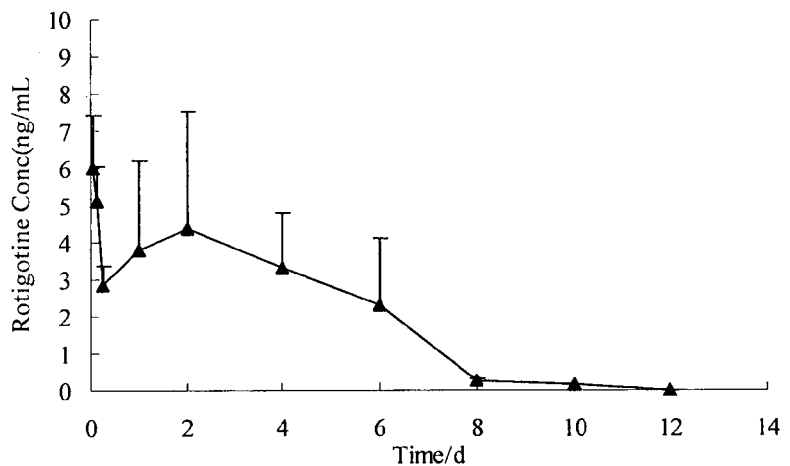
FIG. 19 is the in vivo drug-time curve diagram of the microspheres comprising PLGA 5050 2.5A.

It may be seen from FIG. 19 that, in the earlier release period, the release speed of the PLGA 5050 2.5 A microspheres was faster and the full release period was shorter.

Example 18

Rotigotine Microspheres Comprising a Combination of Two PLGAs with Different Molecular Weights (95:5)

The rotigotine microspheres were prepared from 0.4504 g of rotigotine, and a combination of 0.9973 g of PLGA 7525 4A and 0.0521 g of PLGA 5050 2.5A (with a weight ratio of 95:5) according to the method of EXAMPLE 1.

Example 19

Rotigotine Microspheres Comprising a Combination of Two PLGAs with Different Molecular Weights (50:50)

The rotigotine microspheres were prepared from 0.4489 g of rotigotine, and a combination of 0.5261 g of PLGA 7525 4A and 0.5256 g of PLGA 5050 2.5A (with a weight ratio of 50:50) according to the method of EXAMPLE 1.

Example 20

Rotigotine Microspheres Comprising a Combination of Two PLGAs with Different Molecular Weights (5:95)

The rotigotine microspheres were prepared from 0.4508 g of rotigotine, and a combination of 0.0519 g of PLGA 7525 4A and 0.9968 g of PLGA 5050 2.5A (with a weight ratio of 5:95) according to the method of EXAMPLE 1.

Test Example 8

Influence of Polymer Combinations with Different Weight Ratios on Drug Release of the Microspheres The in vitro release tests were carried out for the microspheres prepared in EXAMPLEs 18-20 according to the method of Test EXAMPLE 1. The in vitro release results are shown in Table 5 and FIGS. 20-22.

TABLE 5

The in vitro release data of the microspheres prepared from a combination of two PLGAs with different molecular weights

| Time (day) | PLGA7525 4A:PLGA 5050 2.5A = 95:5 | | PLGA7525 4A:PLGA 5050 2.5A = 50:50 | | PLGA 7525 4A:PLGA 5050 2.5A = 5:95 | |
| --- | --- | --- | --- | --- | --- | --- |
|  | Cumulative released amount (%) | Daily released amount (%) | Cumulative released amount (%) | Daily released amount (%) | Cumulative released amount (%) | Daily released amount (%) |
| 0.125 | 2.22 | 2.22 | 2.58 | 2.58 | 2.90 | 2.90 |
| 1 | 9.10 | 9.10 | 12.32 | 12.32 | 16.12 | 16.12 |
| 2 | 15.72 | 6.62 | 23.86 | 11.54 | 29.13 | 13.02 |
| 4 | 29.36 | 6.82 | 45.44 | 10.79 | 53.34 | 12.11 |
| 6 | 52.30 | 11.47 | 63.26 | 8.91 | 73.25 | 9.95 |
| 8 | 64.32 | 6.01 | 74.28 | 5.51 | 89.49 | 8.12 |
| 10 | 75.29 | 5.49 | 82.98 | 4.35 | 95.26 | 2.89 |
| 12 | 86.16 | 5.44 | 91.44 | 4.23 | 97.31 | 1.02 |
| 14 | 92.51 | 3.17 | 97.26 | 2.91 | 99.30 | 0.99 |
| 16 | 95.96 | 1.73 | 99.23 | 0.99 |  |  |
| 18 | 98.29 | 1.16 |  |  |  |  |

Figure 20:
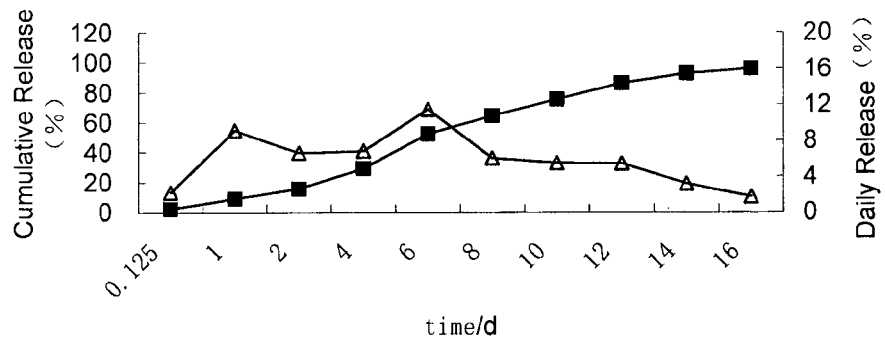
FIG. 20 is the in vitro release diagram of the microspheres comprising two PLGAs with different molecular weights (7525 4A: 5050 2.5A=95:5) prepared in Example 18, in which Δ represents the daily released amount, and ■ represents the cumulative released amount.
Figure 21:
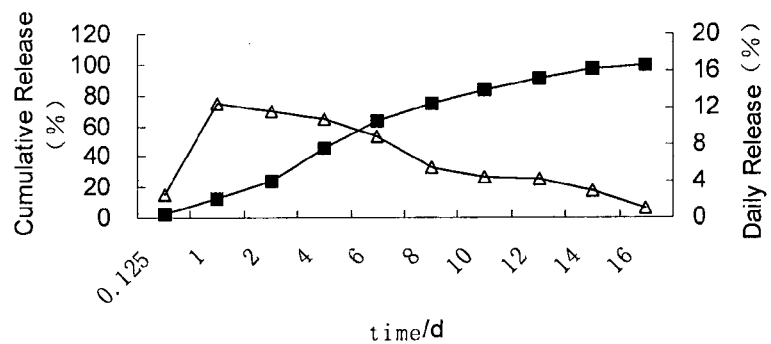
FIG. 21 is the in vitro release diagram of the microspheres comprising two PLGAs with different molecular weights (7525 4A: 5050 2.5A=50:50) prepared in Example 19, in which Δ represents the daily released amount, and ■ represents the cumulative released amount.
Figure 22:
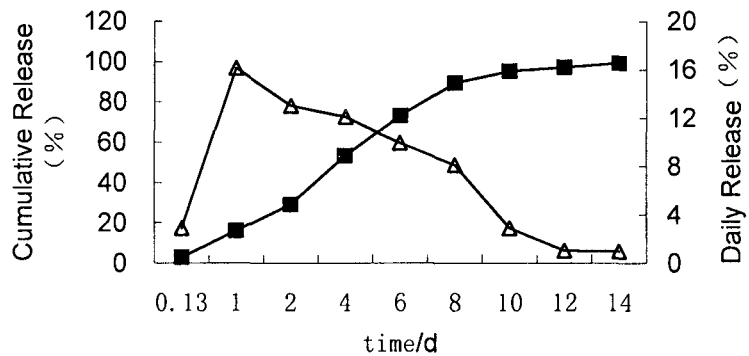
FIG. 22 is the in vitro release diagram of the microspheres comprising two PLGAs with different molecular weights (7525 4A: 5050 2.5A=5:95) prepared in Example 20, in which Δ represents the daily released amount, and ■ represents the cumulative released amount.
Figure 23:
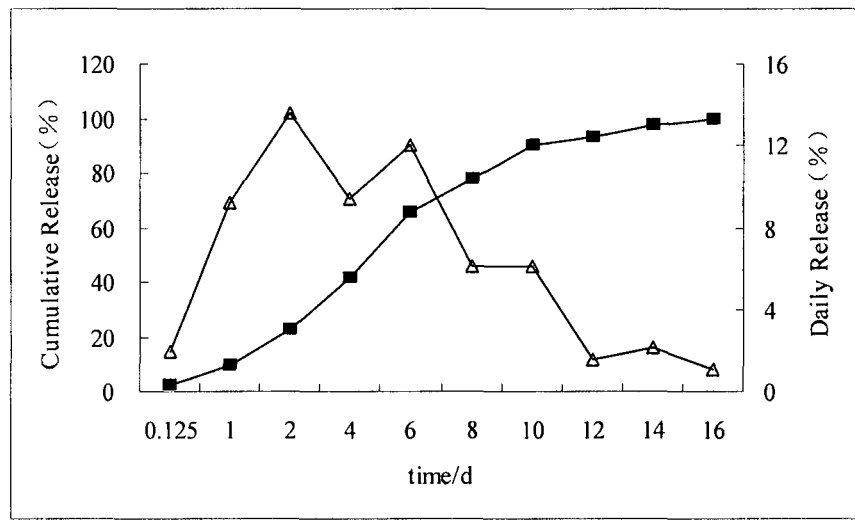
FIG. 23 is the in vitro release diagram of the microspheres comprising stearic acid (1%) and two PLGAs with different molecular weights (7525 4A: 5050 2.5A=50:50) prepared in Example 21, in which Δ represents the daily released amount, and ■ represents the cumulative released amount.

It may be seen from Table 5 and FIGS. 20-22 that, when the content of PLGA 5050 2.5 A in the microspheres was increased from 5% to 95%, the released amounts of rotigotine in 1-4 days were increased, in which the cumulative released amount of rotigotine within 1 day was increased from 9.10% to 16.12% and the cumulative released amount of rotigotine in 4 days was increased from 29.36% to 53.34%. When the weight ratio of PLGA 7525 4A to PLGA 5050 2.5 A in the microspheres was 50:50, compared with the data of EXAMPLE 3 in Table 1, the released amounts of rotigotine in 1-4 days were increased with a stable release period, in which the cumulative released amount of rotigotine within 1 day was increased from 9.53% to 12.32% and the cumulative released amount of rotigotine in 4 days was increased from 22.90% to 45.44%.

Example 21

Rotigotine Microspheres Comprising Stearic Acid (1%) and a Combination of Two PLGAs with Different Molecular Weights (50:50)

The rotigotine microspheres were prepared from 0.4507 g of rotigotine, a combination of 0.5170 g of PLGA 7525 4A and 0.5177 g of PLGA 5050 2.5A (with a weight ratio of 50:50), and 0.0155 g of stearic acid (1%) according to the method of EXAMPLE 1.

Example 22

Microspheres Comprising Stearic Acid (2.5%) and a Combination of Two PLGAs with Different Molecular Weights (50:50)

The rotigotine microspheres were prepared from 0.4491 g of rotigotine, a combination of 0.5060 g of PLGA 7525 4A and 0.5055 g of PLGA 5050 2.5A (with a weight ratio of 50:50), and 0.0371 g of stearic acid (2.5%) according to the method of EXAMPLE 1.

Example 23

Microspheres Comprising Stearic Acid (7.5%) and a Combination of Two PLGAs with Different Molecular Weights (50:50)

The rotigotine microspheres were prepared from 0.4510 g of rotigotine, a combination of 0.4680 g of PLGA 7525 4A and 0.4701 g of PLGA 5050 2.5A (with a weight ratio of 50:50), and 0.1119 g of stearic acid (7.5%) according to the method of EXAMPLE 1.

Example 24

Microspheres Comprising Stearic Acid (10%) and a Combination of Two PLGAs with Different Molecular Weights (50:50)

The rotigotine microspheres were prepared from 0.4503 g of rotigotine, a combination of 0.4479 g of PLGA 7525 4A and 0.4501 g of PLGA 5050 2.5A (with a weight ratio of 50:50), and 0.1520 g of stearic acid (10%) according to the method of EXAMPLE 1.

Example 25

Microspheres Comprising Octanoic Acid (2.5%) and a Combination of Two PLGAs with Different Molecular Weights (50:50)

The rotigotine microspheres were prepared from 0.4490 g of rotigotine, a combination of 0.5101 g of PLGA 7525 4A and 0.5091 g of PLGA 5050 2.5A (with a weight ratio of 50:50), and 0.0380 g of octanoic acid (2.5%) according to the method of EXAMPLE 1.

Example 26

Microspheres Comprising Lignoceric Acid (2.5%) and a Combination of Two PLGAs with Different Molecular Weights (50:50)

The rotigotine microspheres were prepared from 0.4520 g of rotigotine, a combination of 0.5055 g of PLGA 7525 4A and 0.5062 g of PLGA 5050 2.5A (with a weight ratio of 50:50), and 0.0379 g of lignoceric acid (2.5%) according to the method of EXAMPLE 1.

Example 27

Microspheres Comprising Stearic Acid (2.5%) and a Combination of Two PLGAs with Different Molecular Weights (95:5)

The rotigotine microspheres were prepared from 0.4507 g of rotigotine, a combination of 0.9621 g of PLGA 7525 4A and 0.0505 g of PLGA 5050 2.5A (with a weight ratio of 95:5), and 0.0369 g of stearic acid (2.5%) according to the method of EXAMPLE 1.

Example 28

Microspheres Comprising Stearic Acid (2.5%) and a Combination of Two PLGAs with Different Molecular Weights (5:95)

The rotigotine microspheres were prepared from 0.4514 g of rotigotine, a combination of 0.0501 g of PLGA 7525 4A and 0.9610 g of PLGA 5050 2.5A (with a weight ratio of 5:95), and 0.0370 g of stearic acid (2.5%) according to the method of EXAMPLE 1.

Test Example 9

In Vitro Test of the Rotigotine Microspheres Comprising Stearic Acid with Different Contents and a Combination of PLGAs with Different Molecular Weights The in vitro release tests were carried out for the microspheres prepared in EXAMPLEs 21-24 according to the method of Test EXAMPLE 1. The in vitro release results are shown in Table 6 and FIGS. 23-26.

TABLE 6

The in vitro release data of the microspheres comprising stearic acid with different contents and a combination of two PLGAs with different molecular weights

| Time (day) | 7525 4A:5050 2.5A = 50:50 (1% stearic acid) | | 7525 4A:5050 2.5A = 50:50 (2.5% stearic acid) | | 7525 4A:5050 2.5A = 50:50 (7.5% stearic acid) | | 7525 4A:5050 2.5A = 50:50 (10% stearic acid) | |
|---|---|---|---|---|---|---|---|---|
| | Cumulative released amount (%) | Daily released amount (%) | Cumulative released amount (%) | Daily released amount (%) | Cumulative released amount (%) | Daily released amount (%) | Cumulative released amount (%) | Daily released amount (%) |
| 0.125 | 1.96 | 1.96 | 1.02 | 1.02 | 0.91 | 0.91 | 1.13 | 1.13 |
| 1 | 9.19 | 9.19 | 6.32 | 6.32 | 5.18 | 5.18 | 2.87 | 2.87 |
| 2 | 22.80 | 13.61 | 17.78 | 11.46 | 11.46 | 6.28 | 5.78 | 2.91 |
| 4 | 41.53 | 9.36 | 39.17 | 10.69 | 31.83 | 10.18 | 11.24 | 2.73 |
| 6 | 65.49 | 11.98 | 60.00 | 10.42 | 53.15 | 10.66 | 24.45 | 6.61 |
| 8 | 77.74 | 6.12 | 75.37 | 7.68 | 70.41 | 8.63 | 50.47 | 13.01 |
| 10 | 89.90 | 6.08 | 85.71 | 5.17 | 81.12 | 5.36 | 67.76 | 8.65 |
| 12 | 93.04 | 1.57 | 92.61 | 3.45 | 88.77 | 3.83 | 77.49 | 4.86 |
| 14 | 97.38 | 2.17 | 96.14 | 1.77 | 92.85 | 2.04 | 84.64 | 3.58 |
| 16 | 99.56 | 1.09 | 99.22 | 1.54 | 96.26 | 1.70 | 89.79 | 2.57 |
| 18 | | | | | | | 93.67 | 1.94 |
| 20 | | | | | | | 95.82 | 1.08 |

It may be seen by comparing the results in Table 6 and FIGS. 23-26 with those of EXAMPLE 19 in Table 5 that, when the weight ratio of PLGA 7525 4A to PLGA 5050 2.5A was 50:50 and the content of stearic acid in the microspheres was 2.5-7.5%, the burst release effect was significant reduced, and the cumulative drug release curves were much more linear.

Test Example 10

In Vitro Test of the Rotigotine Microspheres Comprising Fatty Acids with Different Molecular Weights and a Combination of PLGAs with Different Molecular Weights The in vitro release tests were carried out for the microspheres prepared in EXAMPLEs 22, 25, and 26 according to the method of Test EXAMPLE 1. The in vitro release results are shown in Table 7 and FIGS. 24, 27, and 28.

Figure 24:
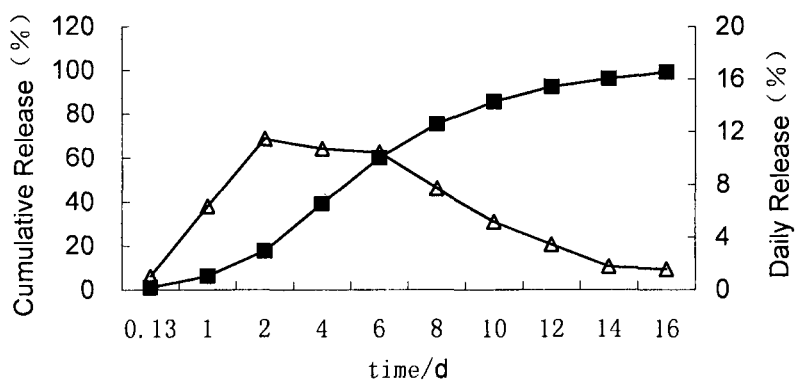
FIG. 24 is the in vitro release diagram of the microspheres comprising stearic acid (2.5%) and two PLGAs with different molecular weights (7525 4A: 5050 2.5A=50:50) prepared in Example 22, in which Δ represents the daily released amount, and ■ represents the cumulative released amount.
Figure 25:
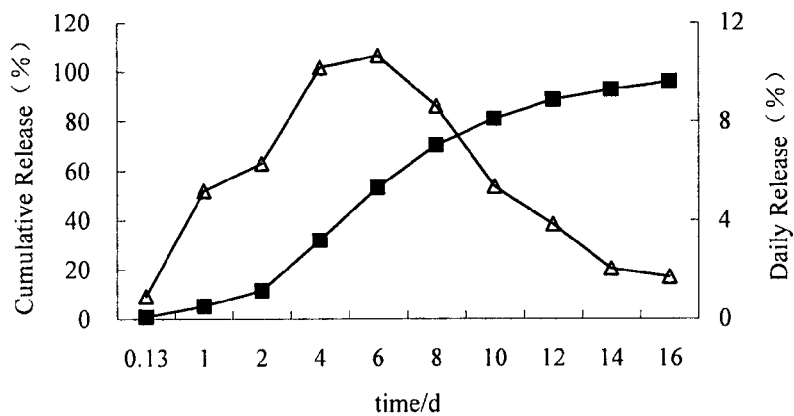
FIG. 25 is the in vitro release diagram of the microspheres comprising stearic acid (7.5%) and two PLGAs with different molecular weights (7525 4A: 5050 2.5A=50:50) prepared in Example 23, in which Δ represents the daily released amount, and ■ represents the cumulative released amount.
Figure 26:
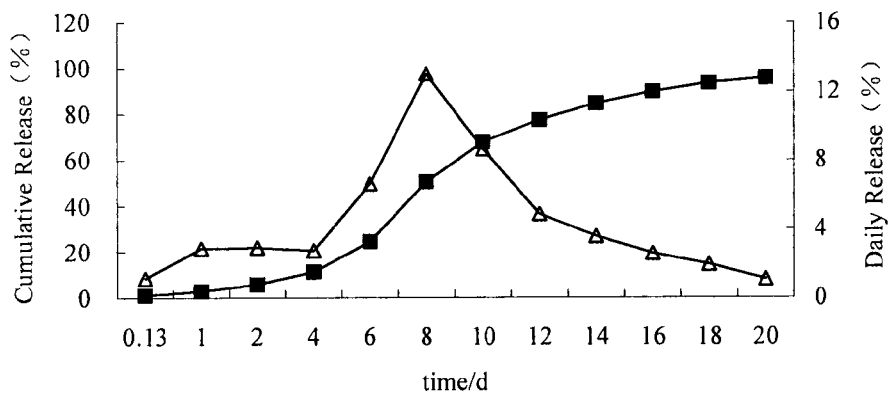
FIG. 26 is the in vitro release diagram of the microspheres comprising stearic acid (10%) and two PLGAs with different molecular weights (7525 4A: 5050 2.5A=50:50) prepared in Example 24, in which Δ represents the daily released amount, and ■ represents the cumulative released amount.
Figure 27:
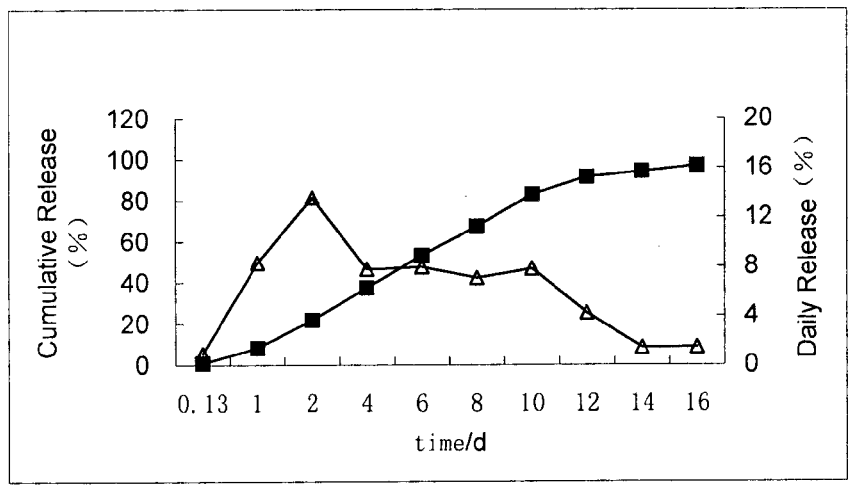
FIG. 27 is the in vitro release diagram of the microspheres comprising octanoic acid (2.5%) and two PLGAs with different molecular weights (7525 4A: 5050 2.5A=50:50) prepared in Example 25, in which Δ represents the daily released amount, and ■ represents the cumulative released amount.
Figure 28:
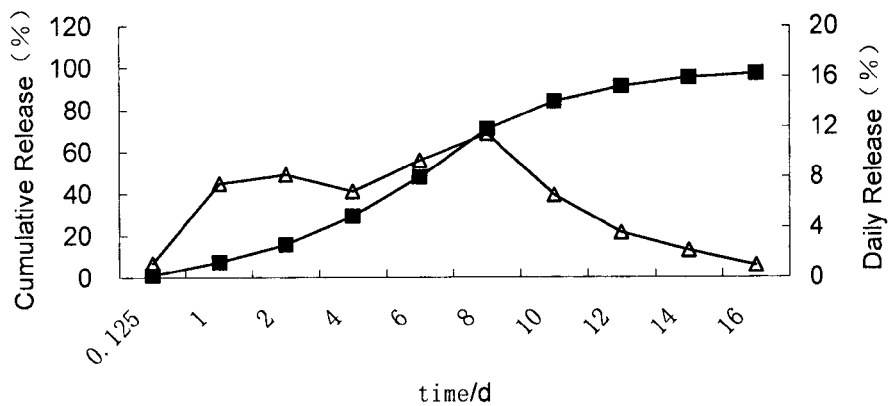
FIG. 28 is the in vitro release diagram of the microspheres comprising lignoceric acid (2.5%) and two PLGAs with different molecular weights (7525 4A: 5050 2.5A=50:50) prepared in Example 26, in which Δ represents the daily released amount, and ■ represents the cumulative released amount.

It may be seen by comparing the results in Table 7 and FIGS. 24, 27, 28 with those of EXAMPLE 19 in Table 5 that, when octanoic acid, stearic acid and lignoceric acid with a content of 2.5% respectively were added to the formulation, the burst release was reduced, and the drug release curves tended to be more linear, which indicates that all of the fatty acids having 8-24 carbon atoms may meet the requirement of stable drug release.

Test Example 11

In Vitro Test of the Rotigotine Microspheres Comprising Stearic Acid (2.5%) and a Combination of PLGAs with Different Molecular Weights in Different Weight Ratios The in vitro release tests were carried out for the microspheres prepared in EXAMPLES 22, 27, and 28 according to the method of Test EXAMPLE 1. The in vitro release results are shown in Table 8 and FIGS. 24, 29, and 30.

TABLE 7

The in vitro release data of the microspheres comprising fatty acids with different molecular weights and a combination of PLGAs with different molecular weights

| Time (day) | 7525 4A:5050 2.5A = 50:50 (2.5% octanoic acid) | | 7525 4A:5050 2.5A = 50:50 (2.5% stearic acid) | | 7525 4A:5050 2.5A = 50:50 (2.5% lignoceric acid) | |
|---|---|---|---|---|---|---|
| | Cumulative released amount (%) | Daily released amount (%) | Cumulative released amount (%) | Daily released amount (%) | Cumulative released amount (%) | Daily released amount (%) |
| 0.125 | 0.92 | 0.92 | 1.02 | 1.02 | 1.13 | 1.13 |
| 1 | 8.27 | 8.27 | 6.32 | 6.32 | 7.48 | 7.48 |
| 2 | 21.86 | 13.59 | 17.78 | 11.46 | 15.66 | 8.18 |
| 4 | 37.41 | 7.77 | 39.17 | 10.69 | 29.35 | 6.85 |
| 6 | 53.26 | 7.93 | 60.00 | 10.42 | 48.02 | 9.33 |
| 8 | 67.35 | 7.04 | 75.37 | 7.68 | 70.91 | 11.45 |
| 10 | 82.98 | 7.81 | 85.71 | 5.17 | 84.08 | 6.59 |
| 12 | 91.44 | 4.23 | 92.61 | 3.45 | 91.22 | 3.57 |
| 14 | 94.26 | 1.41 | 96.14 | 1.77 | 95.54 | 2.16 |
| 16 | 97.16 | 1.45 | 99.22 | 1.54 | 97.49 | 0.98 |

TABLE 8

The in vitro release data of the microspheres comprising stearic acid and a combination of PLGAs with different molecular weights in different weight ratios

| Time (day) | 7525 4A:5050 2.5A = 50:50 (2.5% stearic acid) | | 7525 4A:5050 2.5A = 95:5 (2.5% stearic acid) | | 7525 4A:5050 2.5A = 5:95 (2.5% stearic acid) | |
|---|---|---|---|---|---|---|
| | Cumulative released amount (%) | Daily released amount (%) | Cumulative released amount (%) | Daily released amount (%) | Cumulaltive released amount (%) | Daily released amount (%) |
| 0.125 | 1.02 | 1.02 | 0.96 | 0.96 | 1.24 | 1.24 |
| 1 | 6.32 | 6.32 | 5.19 | 5.19 | 11.18 | 11.18 |
| 2 | 17.78 | 11.46 | 10.46 | 5.27 | 24.13 | 12.95 |
| 4 | 39.17 | 10.69 | 25.47 | 7.50 | 50.45 | 13.16 |
| 6 | 60.00 | 10.42 | 44.25 | 9.39 | 70.25 | 9.90 |
| 8 | 75.37 | 7.68 | 66.29 | 11.02 | 84.49 | 7.12 |
| 10 | 85.71 | 5.17 | 79.25 | 6.48 | 93.26 | 4.39 |
| 12 | 92.61 | 3.45 | 88.19 | 4.47 | 96.10 | 1.42 |
| 14 | 96.14 | 1.77 | 94.51 | 3.16 | 99.28 | 1.59 |
| 16 | 99.22 | 1.54 | 98.80 | 2.14 | | |

Figure 29:
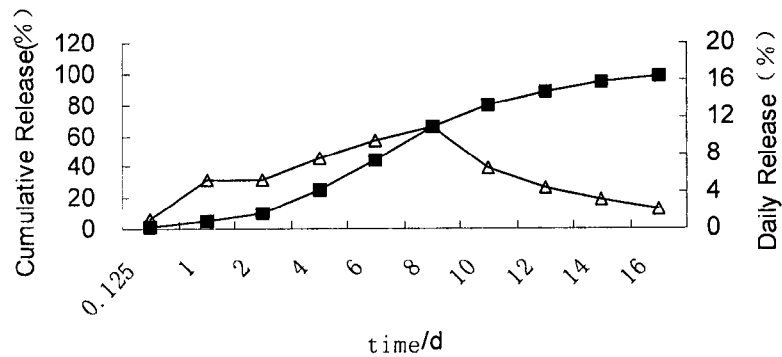
FIG. 29 is the in vitro release diagram of the microspheres comprising stearic acid (2.5%) and two PLGAs with different molecular weights (7525 4A: 5050 2.5A=95:5) prepared in Example 27, in which Δ represents the daily released amount, and ■ represents the cumulative released amount.
Figure 30:
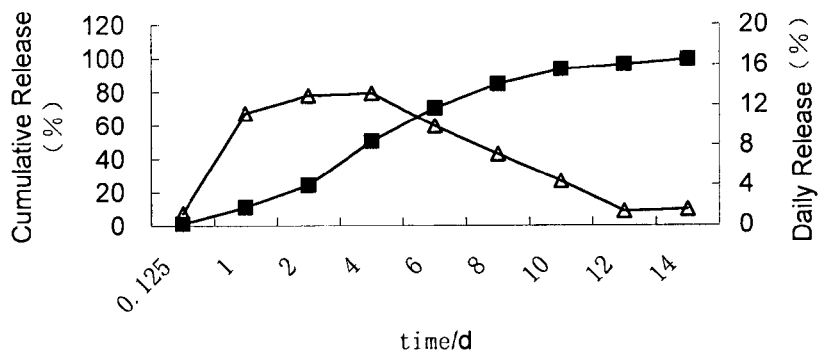
FIG. 30 is the in vitro release diagram of the microspheres comprising stearic acid (2.5%) and two PLGAs with different molecular weights (7525 4A: 5050 2.5A=5:95) prepared in Example 28, in which Δ represents the daily released amount, and ■ represents the cumulative released amount.

It may be seen from Table 8 and FIGS. 29 and 30 that, when the content of stearic acid was 2.5% and the weight ratio of PLGA 7525 4A to PLGA 5050 2.5A was 95:5, the drug release amount in 1-4 days was slightly low; when the weight ratio of PLGA 7525 4A to PLGA 5050 2.5A was 5:95, the drug release amount in 1-4 days was slightly high, and on the 10$^{th}$ day, the cumulative released amount reached 93.26% with a short release period; and when the weight ratio of PLGA 7525 4A to PLGA 5050 2.5A was 50:50, the drug release was more stable, and the drug may be sustainably released for 14 days.

Test Example 12

Figure 31:
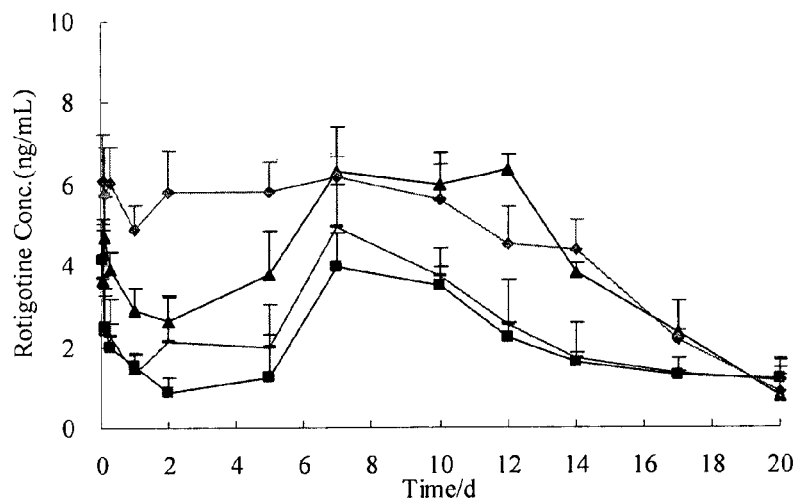
FIG. 31 is the in vivo drug-time curve diagram of the microspheres comprising stearic acid (2.5%) and two PLGAs with different molecular weights in different weight ratios, in which ♦ represents the in vivo drug-time curve diagram of the microspheres (7525 4A: 5050 2.5A=50:50) (2.5% stearic acid), ▲ represents the in vivo drug-time curve diagram of the microspheres (7525 4A: 5050 2.5A=70:30) (2.5% stearic acid), ------ represents the in vivo drug-time curve diagram of the microspheres (7525 4A: 5050 2.5A=80:20) (2.5% stearic acid), and ■ represents the in vivo drug-time curve diagram of the microspheres (7525 4A: 5050 2.5A=90:10) (2.5% stearic acid).

In Vivo Test of the Microspheres with a Drug-Loading Rate Comprising Stearic Acid (2.5%) and a Combination of PLGA 7525 4a and PLGA 5050 2.5a with Different Weight Ratios The microspheres were prepared according to EXAMPLE 8, but with different weight ratios of PLGA 7525 4A to PLGA 5050 2.5A of 90:10, 80:20, 70:30 and 50:50. The in vivo release tests were carried out for the microspheres according to the method of Test EXAMPLE 2. The results are shown in FIG. 31.

It may be seen from the in vivo release (FIG. 31) that, after two PLGAs with different weight ratios were mixed with different weight ratios, with increasing content of PLGA 5050 2.5A, the drug release amounts of the microspheres in 1-4 days were increased, and the in vivo release curve tended to be more stable; and when the weight ratio of PLGA 7525 4A to PLGA 5050 2.5A was 50:50, the in vivo release curve was more stable without significant burst release effect.

As indicated from the above results, two PLGAs with different weight ratios were mixed in different weight ratios, thus effectively overcoming the defects of a single PLGA. That is, PLGA with a molecular weight of 15000-30000 (PLGA 2.5A) may increase the drug release amount of the microspheres in 1-4 days, and PLGA with a molecular weight of 42000-75000 (PLGA 4A) may prolong the drug release period, thus obtaining microspheres with more stable in vivo drug release.

Test Example 13

In Vitro Test of the Microspheres with a Drug-Loading Rate Comprising Stearic Acid (2.5%) and a Combination of PLGA 7525 5a and PLGA 5050 2.5a with Different Weight Ratios The microspheres were prepared according to EXAMPLE 8, but with different weight ratios of PLGA 7525 5A to PLGA 5050 2.5A of 90:10, 80:20 and 70:30. The in vitro release tests were carried out for the microspheres according to the method of Test EXAMPLE 1. The in vitro release data are shown in Table 9.

TABLE 9

The in vitro release data of the microspheres comprising stearic acid and a combination of PLGA 7525 5A and PLGA 5050 2.5A with different molecular weights

| Time (day) | 7525 5A:5050 2.5A = 90:10 (2.5% stearic acid) | | 7525 5A:5050 2.5A = 80:20 (2.5% stearic acid) | | 7525 5A:5050 2.5A = 70:30 (2.5% stearic acid) | |
|---|---|---|---|---|---|---|
| | Cumulative released amount (%) | Daily released amount (%) | Cumulative released amount (%) | Daily released amount (%) | Cumulative released amount (%) | Daily released amount (%) |
| 0.125 | 1.44 | 1.44 | 1.53 | 1.53 | 1.61 | 1.61 |
| 1 | 4.28 | 4.28 | 6.23 | 6.23 | 7.64 | 7.64 |
| 2 | 8.73 | 4.45 | 11.70 | 5.47 | 15.74 | 7.09 |

TABLE 9-continued

The in vitro release data of the microspheres comprising stearic acid and a combination of PLGA 7525 5A and PLGA 5050 2.5A with different molecular weights

| Time (day) | 7525 5A:5050 2.5A = 90:10 (2.5% stearic acid) | | 7525 5A:5050 2.5A = 80:20 (2.5% stearic acid) | | 7525 5A:5050 2.5A = 70:30 (2.5% stearic acid) | |
|---|---|---|---|---|---|---|
| | Cumulative released amount (%) | Daily released amount (%) | Cumulative released amount (%) | Daily released amount (%) | Cumulative released amount (%) | Daily released amount (%) |
| 4 | 24.29 | 7.78 | 28.96 | 8.63 | 30.21 | 7.74 |
| 6 | 42.41 | 9.06 | 43.30 | 7.17 | 47.89 | 8.84 |
| 8 | 63.49 | 10.54 | 65.68 | 11.19 | 63.17 | 7.64 |
| 10 | 75.38 | 5.95 | 74.35 | 4.33 | 72.48 | 4.66 |
| 12 | 84.65 | 4.64 | 80.81 | 3.23 | 81.97 | 4.75 |
| 14 | 90.45 | 2.90 | 90.57 | 4.88 | 89.30 | 3.66 |
| 16 | 94.83 | 2.19 | 95.78 | 2.61 | 92.56 | 1.63 |
| 18 | 97.87 | 1.52 | 98.21 | 1.22 | 94.65 | 1.05 |
| 20 | | | | | 95.81 | 0.58 |

It may be seen from Table 9 that, after PLGA (7525 5A) and PLGA (5050 2.5A) were mixed with different weight ratios, the drug release characteristics of the prepared microspheres were similar to those of the microspheres prepared from PLGA (7525 4A) and PLGA (5050 2.5A). With increasing content of PLGA (5050 2.5A) in the microspheres, the drug release amount of the microspheres in 1-4 days were increased accordingly. When the weight ratio of PLGA 7525 5A to PLGA 5050 2.5A was varied from 90:10 to 70:30, the cumulative released amount within 1 day was increased from 4.28% to 7.64%, and the cumulative released amount in 4 days was increased from 24.29% to 30.21%. Because the microspheres contain 2.5% stearic acid, the release amounts of the microspheres in 0.125 day and 1 day were smaller, which indicates that the in vivo burst release of the microspheres was smaller.

Test Example 14

In Vitro-In Vivo Correlation Test of the Rotigotine Microspheres

Figure 32:
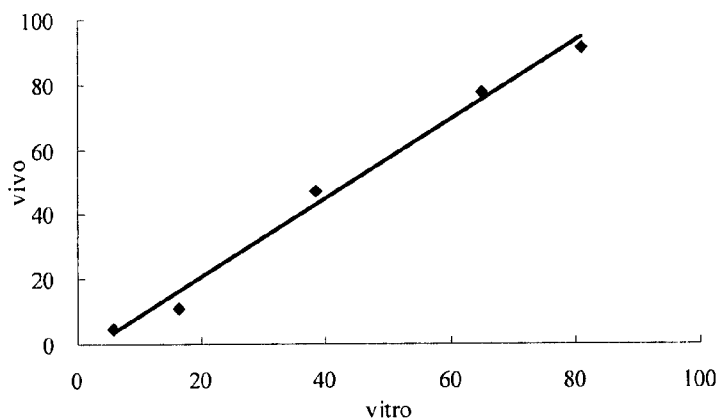
FIG. 32 is the in vitro-in vivo correlation diagram of the rotigotine microspheres prepared in Example 22.

The correlation diagram was plotted with the in vitro accumulative release data and the in vivo release data of the microspheres prepared in EXAMPLE 22, as shown in FIG. 32 (the linear equation: y=1.2137x-3.7464, r=0.9943). It may be seen from FIG. 32 that, the in vitro drug release time and the in vivo absorption percent of the rotigotine microspheres have a good correlation, which indicates that the selected in vitro release condition for evaluating the in vitro release of the microspheres may be used to predict the in vivo release profile of the microspheres.

Test Example 15

The Determination of the Molecular Weight of PLGA

Instrument and Reagent

Agilent 1100 high performance liquid chromatograph (comprising a quatpump, a column oven, an automatic sampler, a RID detector and HP-ChemStation with GPC software); chromatographic column: Styragel® HT3 (7.8×300 mm, 10 μm, molecular weight range: 500-30000). Styragel® 6E (7.8×300 mm, 10 μm, molecular weight range: 5000-600000); tetrahydrofuran (chromatographic pure, SK CHEMICAL, G6EE3H); polystyrene molecular weight standard (Fluka, 1226627); Sample: PLGA 7525 5A, PLGA 7525 4A, PLGA 5050 2.5A (Lakeshore Biomaterials, Inc.).

The molecular weights of the samples were determined using the size exclusion chromatography. Because the polymer PLGA was liposoluble and has no ultraviolet absorption, the samples were tested on a differential refractive index detector using tetrahydrofuran as the solvent and the mobile phase. Because the molecular weight ($M_w$) of the polymer PLGA was about 50,000, the molecular weight range of the selected chromatographic column included this range, and the molecular weight distribution range of the samples to be measured was in the middle of the molecular weight range of the selected chromatographic column. Styragel® HT3 (7.8× 300 mm, 10 μm, molecular weight range: 500-30,000) and Styragel® 6E (7.8×300 mm, 10 μm, molecular weight range: 5,000-600,000) were connected in series for use. Because the property of PLGA is similar to that of polystyrene, a polystyrene mixed standard (molecular weight range: 500-2,500,000) comprising a molecular weight range of the samples available from Fluka Chemical Corp. was selected.

Determination Method

Appropriate amount of the sample was added to a mobile phase to prepare a solution with a concentration of about 1 mg/ml, and vibrated to prepare a test solution. One set of polystyrene molecular weight standard (3 bottles, each bottle comprising a mixed standard of 4 standard molecular weights) was added to the mobile phase to prepare a solution with a concentration of 1.0 mg/ml as a reference solution. The test was carried out on a differential refractive index detector according to the size exclusion chromatography (Chinese Pharmacopeia 2005, vol. II, appendix VH) using gel chromatographic columns and using tetrahydrofuran as the mobile phase with a column temperature of 30° C., a flow rate of 1.0 mL/min and a detector temperature of 35° C. A required amount of acetonitrile was diluted at a factor of 500 with the mobile phase. 20 μl of the diluted solution was injected into the liquid chromatograph, and the chromatogram was recorded, with a theoretical plate number of no less than 10,000 calculated according to the acetonitrile peak.

20 μl of each of the reference solutions was injected into the liquid chromatograph, the chromatogram was recorded, and the regression equation was calculated by the GPC software. 20 μl of the test solution was measured according to the same method, the weight-average molecular weight, the number-average molecular weight and the molecular weight distribution of the sample were calculated by the GPC software. The results are shown in Tables 10, 11, and 12.

TABLE 10

The results of the molecular weight of PLGA

| No. | PLGA 5050 2.5A (kDa) | PLGA 7525 4A (kDa) | PLGA 7525 5A (kDa) |
|---|---|---|---|
| 1 | 24 | 49 | 67 |
| 2 | 23 | 53 | 66 |
| 3 | 23 | 51 | 67 |

The results of PLGA test report from Lakeshore Biomaterials Inc. are shown in Table 11.

TABLE 11

PLGA molecular weight test report

| No. | PLGA 5050 2.5A (kDa) | PLGA 7525 4A (kDa) | PLGA 7525 5A (kDa) |
|---|---|---|---|
| 1 | 26 | 51 | 67 |
| 2 | 26 | 54 | 68 |
| 3 | 28 | 42 | 72 |

TABLE 12

PLGA molecular weight distribution

| PLGA | molecular weight distribution |
|---|---|
| PLGA 5050 2.5A | 15,000-35,000 |
| PLGA 7525 4A | 42,000-58,000 |
| PLGA 7525 5A | 55,000-75,000 |

The molecular weights of certain PLGA are shown in Table 12.

Test Example 16

Batch-to-Batch Consistency

Five batches of the rotigotine microspheres were prepared according to the method of EXAMPLE 3, EXAMPLE 8, EXAMPLE 11, EXAMPLE 12, EXAMPLE 14, and EXAMPLE 16. The in vitro release tests were carried out for the microspheres according to the method of Test EXAMPLE 1.

Figure 33:
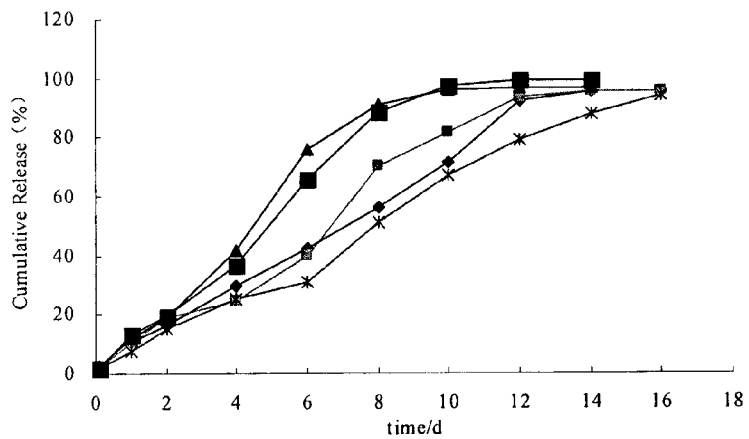
FIG. 33 is the in vitro release diagram of 5 batches microspheres prepared in Example 3.

The in vitro release curves of the 5 batches microspheres prepared in Example 3 are shown in FIG. 33.

Figure 34:
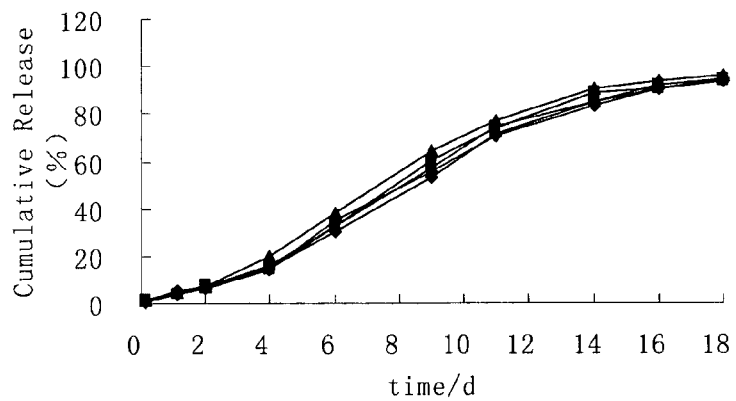
FIG. 34 is the in vitro release diagram of 5 batches microspheres prepared in Example 8.

The in vitro release curves of the 5 batches of microspheres prepared in Example 8 are shown in FIG. 34.

Figure 35:
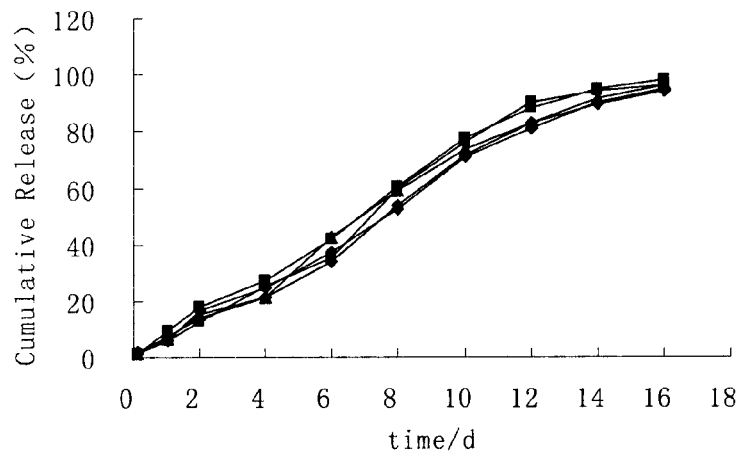
FIG. 35 is the in vitro release diagram of 5 batches microspheres prepared in Example 14.

The in vitro release curves of the 5 batches of microspheres prepared in Example 14 are shown in FIG. 35.

Figure 36:
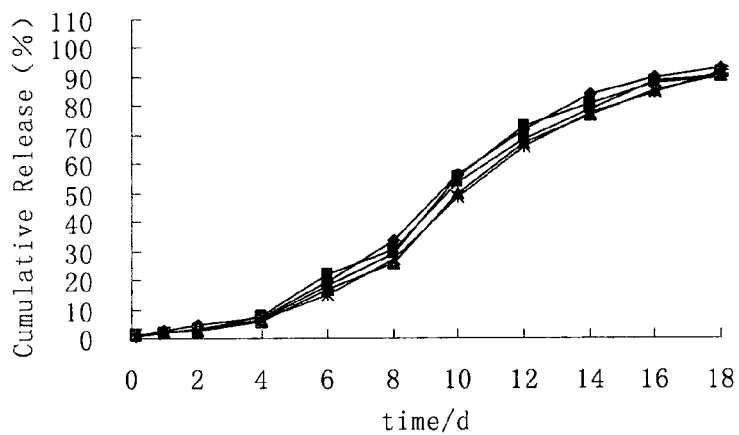
FIG. 36 is the in vitro release diagram of 5 batches microspheres prepared in Example 16.

The in vitro release curves of the 5 batches of microspheres prepared in Example 16 are shown in FIG. 36.

Figure 37:
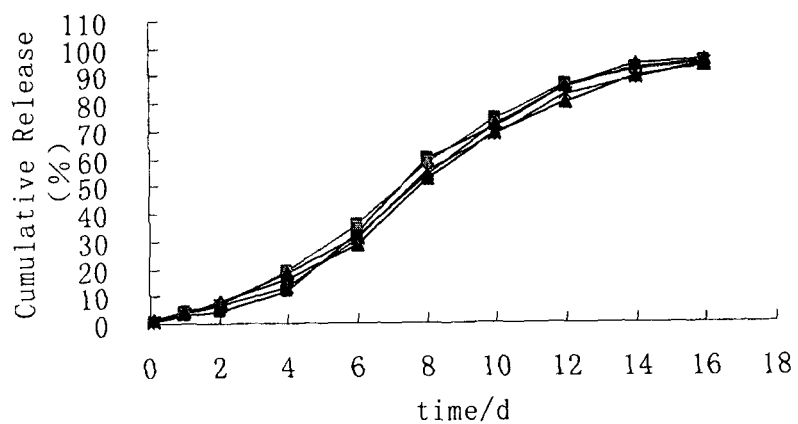
FIG. 37 is the in vitro release diagram of 5 batches microspheres prepared in Example 11.

The in vitro release curves of the 5 batches of microspheres prepared in Example 11 are shown in FIG. 37.

Figure 38:
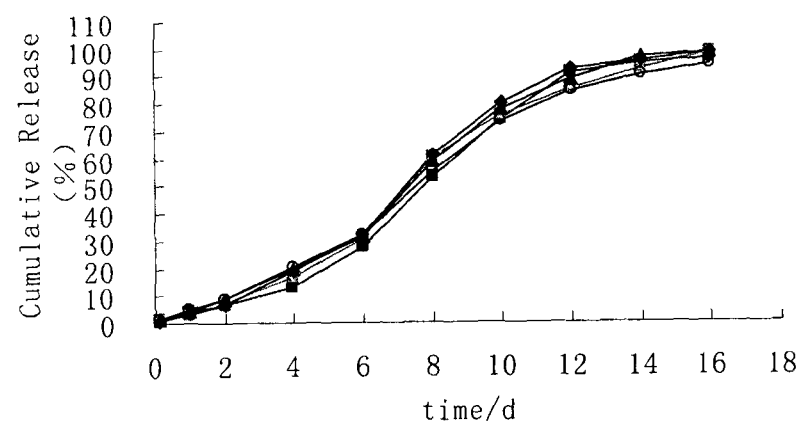
FIG. 38 is the in vitro release diagram of 5 batches microspheres prepared in Example 12.

The in vitro release curves of the 5 batches of microspheres prepared in Example 12 are shown in FIG. 38.

What claimed is:

1. A composition comprising rotigotine or a pharmaceutically acceptable salt thereof; at least one poly(lactide-co-glycolide) (PLGA); and at least one fatty acid, wherein the rotigotine or a pharmaceutically acceptable salt thereof is about 20-40% in weight relative to the total weight of the composition, and wherein the at least one fatty acid is about 1-15% in weight relative to the total weight of the composition.

2. The composition of claim 1, wherein the composition is in the form of microspheres.

3. The composition of claim 2, wherein the at least one PLGA is about 45-79% in weight relative to the total amount of the composition.

4. The composition of claim 3, wherein the pharmaceutically acceptable salt is formed with an inorganic acid or an organic acid.

5. The composition of claim 4, wherein the inorganic acid is chosen from hydrochloric acid, sulphuric acid, phosphoric acid, and nitric acid.

6. The composition of claim 4, wherein the organic acid is chosen from citric acid, fumaric acid, maleic acid, acetic acid, benzoic acid, lactic acid, methane sulfonic acid, naphthalene sulfonic acid, and toluene-p-sulfonic acid.

7. The composition of claim 4, wherein the organic acid is an acidic amino acid chosen from glutamic acid and aspartic acid.

8. The composition of claim 3, wherein the rotigotine or a pharmaceutically acceptable salt thereof is about 20-40%, the at least one PLGA is about 57.5-72.5%, and the fatty acid is about 2.5-7.5% relative to the total weight of the composition.

9. The composition of claim 8, wherein the rotigotine or a pharmaceutically acceptable salt thereof is about 20-40%, the at least one PLGA is about 57.5-77.5%, and the fatty acid is about 2.5% relative to the total weight of the composition.

10. The composition of claim 3, wherein the rotigotine or a pharmaceutically acceptable salt thereof is about 30%, the at least one PLGA is about 55-69%, and the fatty acid is about 1-15% relative to the total weight of the composition.

11. The composition of claim 10, wherein the rotigotine or a pharmaceutically acceptable salt thereof is about 30%, the at least one PLGA is about 62.5-67.5%, and the fatty acid is about 2.5-7.5% relative to the total weight of the composition.

12. The composition of claim 3, wherein the at least one PLGA is about 5,000-100,000 Da in molecular weight.

13. The composition of claim 12, wherein the at least one PLGA has a polymerization ratio of lactide to glycolide ranging from about 95:5 to 5:95.

14. The composition of claim 13, wherein the polymerization ratio of lactide to glycolide ranges from about 75:25 to 25:75.

15. The composition of claim 3, wherein the at least one fatty acid is chosen from fatty acids having 8-24 carbon atoms.

16. The composition of claim 15, wherein the at least one fatty acid is chosen from stearic acid, palmitic acid, oleic acid, decanoic acid, octanoic acid, and lignoceric acid.

17. The composition of claim 3, wherein the at least one PLGA comprises a first PLGA and a second PLGA, wherein the first PLGA has a molecular weight of about 42,000-75,000 Da, the second PLGA has a molecular weight of about 15,000-35,000 Da, and the weight ratio of the first PLGA and the second PLGA is about 95:5 to 5:95.

18. The composition of claim 17, wherein the first PLGA is chosen from PLGA (7525 4A) and PLGA (7525 5A), and the second PLGA is PLGA (5050 2.5A).

19. The composition of claim 18, wherein the weight ratio of the first PLGA and the second PLGA is about 50:50.

20. The composition of claim 17, wherein the rotigotine or a pharmaceutically acceptable salt thereof is about 20-40%, the amount of the first PLGA and the second PLGA is about 57.5-72.5%, and the fatty acid is about 2.5-7.5% relative to the total weight of the composition.

21. The composition of claim 20, wherein the rotigotine or a pharmaceutically acceptable salt thereof is about 20-40%, the amount of the first PLGA and the second PLGA is about 57.5-77.5%, and the fatty acid is about 2.5% relative to the total weight of the composition.

22. The composition of claim 17, wherein the rotigotine or a pharmaceutically acceptable salt thereof is about 30%, the amount of the first PLGA and the second PLGA is about 55-69%, and the fatty acid is about 1-15% relative to the total weight of the composition.

23. The composition of claim 22, wherein the rotigotine or a pharmaceutically acceptable salt thereof is about 30%, the amount of the first PLGA and the second PLGA is about 62.5-67.5%, and the fatty acid is about 2.5-7.5% relative to the total weight of the composition.

24. The composition of claim 23, wherein the rotigotine or a pharmaceutically acceptable salt thereof is about 30%, the amount of the first PLGA and the second PLGA is about 67.5%, and the fatty acid is about 2.5% relative to the total weight of the composition.

25. A method of treating Parkinson's disease comprising administering an effective amount of the composition of claim 1 to a subject in need thereof.

26. A method of treating a disease Associated with dopamine receptors and/or Parkinson's disease comprising administering an effective amount of the composition of claim 24 to a subject in need thereof.

27. The method of claim 26, wherein the composition of claim 24 is administered parenterally.

* * * * *